United States Patent
Spodsberg et al.

(10) Patent No.: US 11,889,847 B2
(45) Date of Patent: Feb. 6, 2024

(54) METHOD FOR PRODUCING A COFFEE EXTRACT EMPLOYING ENZYMES HAVING BETA-1,3-GALACTANASE ACTIVITY

(71) Applicant: Novozymes A/S, Bagsvaerd (DK)

(72) Inventors: Nikolaj Spodsberg, Bagsvaerd (DK); Kristian Bertel Roemer M Krogh, Bagsvaerd (DK); Rune Nygaard Monrad, Hilleroed (DK); Jens Ekloef, Copenhagen (DK); Louise Rasmussen, Helsinge (DK); Gitte Budolfsen Lynglev, Frederiksberg (DK); Laure Coulomb, Toulouse (FR)

(73) Assignee: Novozymes A/S, Bagsvaerd (DK)

( * ) Notice: Subject to any disclaimer, the term of this patent is extended or adjusted under 35 U.S.C. 154(b) by 249 days.

(21) Appl. No.: 14/909,576

(22) PCT Filed: Aug. 15, 2014

(86) PCT No.: PCT/EP2014/067504
§ 371 (c)(1),
(2) Date: Feb. 2, 2016

(87) PCT Pub. No.: WO2015/022428
PCT Pub. Date: Feb. 19, 2015

(65) Prior Publication Data
US 2016/0249635 A1 Sep. 1, 2016

(30) Foreign Application Priority Data

Aug. 15, 2013 (EP) ..................... 13180578

(51) Int. Cl.
*A23F 5/24* (2006.01)
*A23F 5/36* (2006.01)
*C12N 9/24* (2006.01)

(52) U.S. Cl.
CPC ............... *A23F 5/246* (2013.01); *A23F 5/36* (2013.01); *C12N 9/2402* (2013.01); *C12Y 302/01145* (2013.01); *C12Y 302/01181* (2015.07)

(58) Field of Classification Search
CPC .... A23F 5/246; A23F 5/36; C12Y 302/01145; C12Y 302/01181
See application file for complete search history.

(56) References Cited

U.S. PATENT DOCUMENTS

| | | |
|---|---|---|
| 4,508,745 A | 4/1985 | Fulger et al. |
| 4,983,408 A | 1/1991 | Colton |
| 5,714,183 A | 2/1998 | Nicolas |
| 2007/0248731 A1* | 10/2007 | Curti .............. A23F 5/02 426/384 |
| 2011/0182862 A1* | 7/2011 | Green ................ A01N 63/04 424/93.5 |

FOREIGN PATENT DOCUMENTS

| | | | | |
|---|---|---|---|---|
| EP | 1600461 A1 | 11/2005 | | |
| EP | 1844661 A1 | 10/2007 | | |
| JP | 2006211938 | 8/2006 | | |
| WO | WO 2003012110 | * | 2/2003 | ............... C12N 1/21 |
| WO | 2007011531 A1 | 1/2007 | | |
| WO | 2011085747 A1 | 7/2011 | | |

OTHER PUBLICATIONS

Kotake et al. "Endo beta 1,3 galactanase from Winter Mushroom *Flammulina velutipes*" The Journal of Biological Chemistry vol. 286 No. 31 p. 27848-27854 Aug. 5, 2011. (Year: 2011).*
Kobayashi et al. JP 2005-245303 Sep. 1, 2005 22 pages (Year: 2005).*
Ellison et al. "Massive changes in genome architecture accompany the transition of self-fertility in the filamentous fungus *Neurospora tetrasperma*" Genetics vol. 189 pp. 55-69 2011 (Year: 2011).*
GenomeNet https://www.genome.jp/dbget-bin/www_bget?tr:G4UQB7_NEUT9. (Year: 2011).*
Nunes et al. Journal of Agricultural and Food Chemistry 2002 vol. 50 pp. 1429-1434 (Year: 2002).*
Iwai et al. "Isolation and Characterization of β, 1→3, Galactanase from the strain of A. Niger No. 232" 2004 (Year: 2004).*
Hashimoto et al, 1971, Nippon Nogei, vol. 45, pp. 147-150.
Iwai et al, 2004, Japan J Food Microbiol, vol. 21, No. 1, pp. 52-61.
Kotake et al, 2011, J Biol Chem, vol. 286, No. 31, pp. 27848-27854.
Salzmann et al, 1991, Enzyme Handbook, pp. 1-3.
Van De Vis, 1994, vol. 7, No. 125, pp. 1-170.
Brenda, 2015, Brenda Information , The comprehensive Enzyme Information System, pp. 1-130.
Dekker et al., 1985, Biosy Biodegrade Wood Compo, pp. 505-533.
Fujita et al, 1996, J Antibact Antifung Agents, vol. 24, No. 12, pp. 773-782.
Hashimoto et al, 1969, Studies on the Enzyme Treatment of Coffee Beans Part III, vol. 43, No. 12, pp. 831-836.
Kotake et al, 2009, Biosci Biotech Biochem, vol. 73, No. 10, pp. 2303-2309.
Redgwell et al, 2002, Carbo Res, vol. 337, No. 3, pp. 239-253.
Tsumuraya et al, 1990, J Biol Chem, vol. 265, pp. 7207-7215.

* cited by examiner

*Primary Examiner* — Felicia C Turner
(74) *Attorney, Agent, or Firm* — Yoshimi D. Barron

(57) ABSTRACT

The present invention relates to a method for producing a coffee extract which comprises use of an enzyme having β-1,3-galactanase activity and to a coffee extract which comprises at least 20% based on the total weight of soluble coffee solids of total galactose.

10 Claims, No Drawings
Specification includes a Sequence Listing.

METHOD FOR PRODUCING A COFFEE EXTRACT EMPLOYING ENZYMES HAVING BETA-1,3-GALACTANASE ACTIVITY

CROSS-REFERENCE TO RELATED APPLICATIONS

This application is a 35 U.S.C. 371 national application of PCT/EP2014/067504 filed Aug. 15, 2014, which claims priority or the benefit under 35 U.S.C. 119 of European application no. 13180578.0 filed Aug. 15, 2013 the contents of which are fully incorporated herein by reference.

REFERENCE TO SEQUENCE LISTING

This application contains a Sequence Listing in computer readable form. The computer readable form is incorporated herein by reference.

FIELD OF THE INVENTION

The present invention relates to enzyme-assisted production of coffee extracts.

BACKGROUND OF THE INVENTION

Coffee extract, i.e., an aqueous solution of soluble solids extracted from the coffee bean, has various industrial applications. It is used, e.g., in the manufacture of instant coffee; in ready-to-drink coffee products such as canned coffee and bottled coffee drinks; and in non-beverage applications such as instant desserts, confectionery products and flavours.

Commercial coffee extracts are typically produced by stagewise thermal processing, a combination of wetting, extraction and hydrolysis stages, which solubilizes a high percentage of the roast and ground coffee solids. Very high temperatures are required to effect thermal hydrolysis and this may lead to off-flavours and to cost and capital intensive processes.

Use of various different enzymes in the production of coffee extracts to improve product quality and process economics has been suggested (see, e.g., U.S. Pat. No. 4,983,408, WO2007/011531, U.S. Pat. No. 5,714,183). Use of mannanase in the production of a soluble coffee extract has been disclosed in, e.g., WO2007/011531 and U.S. Pat. No. 5,714,183.

EP1600461A1 discloses enzymatic extraction of arabinogalactan from green and roasted coffee beans, where the arabinogalactan is minimally degraded.

Cloning and expression in *Pichia pastoris* of exo-beta-1, 3-galactanase from *Irpex lacteus* has been described in Kotake et al. (2009), Biosci. Biotech. Biochem., 73:2303-2309.

It is an object of the present invention to obtain coffee extracts having a high yield of soluble solids.

SUMMARY OF THE INVENTION

The present inventors have shown that enzyme assisted coffee extraction can solubilize carbohydrates more selectively and efficiently than the conventional processes. This has the potential to save beans and reduce the cost of operations. Further, possible enzymatic degradation of the spent grounds may make them more applicable for utilization in ethanol production or as substrate for sugars/polymers. Enzyme assisted coffee extraction therefore also has the potential of upgrading the side streams from the extraction process.

The inventors have found that incubation of roasted ground coffee beans or partially extracted coffee beans with β-1,3-galactanase results in a substantial release of soluble coffee solids. The results obtained indicate that the yield of soluble solids is considerably higher when using a β-1,3-galactanase as compared to a β-1,4-galactanase. The yield of soluble solids is at least the same when incubating with a β-1,3-galactanase as when incubating with a mannanase, and for most of the β-1,3-galactanases tested, the yield of soluble solids is higher than when incubating with mannanase.

The inventors found that incubation with β-1,3-galactanase released more colour per dry matter than incubation with mannanase, i.e. the extracts appeared darker. This may indicate a better release of flavour compounds when using a β-1,3-galactanase as compared to mannanase. Without wishing to be bound by theory, this could be due to capture of such compounds within the galactan matrix or due to their presence in melanoidin complexes released into the supernatant by the beta-1,3-galactanases. The difference in the colour release by the different enzymatic treatments was determined by measurement of absorbance at 361 nm. But the difference in colour was also clearly visible in the coffee extracts and could easily be detected by the naked eye.

The total sugar composition in the extracts was analysed and it was shown that incubation with β-1,3-galactanase resulted in solubilisation of a substantial amount of oligosaccharides comprising galactose. When β-1,3-galactanase having primarily endo-β-1,3-galactanase activity was used, most of the released galactose was released as oligosaccharides. A higher amount in the coffee extract of oligosaccharides as compared to monosaccharides will contribute more to viscosity and mouth-feel. Also, the arabinogalactan oligosaccharides in the coffee extract will probably have a prebiotic effect.

The solubilized oligosaccharides resulting from the incubation of the spent coffee grounds with beta-1,3-galactanase were shown to have a high ratio of galactose to arabinose.

The molecular weight distribution of the coffee extracts was analysed. Coffee extracts resulting from coffee grounds incubated with beta-1,3-galactanases resulted in the coffee solids having a higher average molecular weight compared to coffee grounds incubated with mannanase.

The inventors also found that debranching of arabinogalactan substrate potentiates the activity of the beta-1,3-galactanases used. I.e., the decrease of side chains on the substrate increases the beta-1,3-galactanase activity. This is relevant for enzymatic treatment of roasted coffee since roasting results in debranching of the arabinogalactan in the coffee beans.

The present invention relates to a method for producing a coffee extract, comprising the steps:
  a. providing roast and ground coffee beans;
  b. adding to said coffee beans water and an enzyme having β-1,3-galactanase activity;
  c. incubating to make an aqueous coffee extract; and
  d. separating the coffee extract from the extracted coffee beans.

The inventors found that the yield of soluble solids was substantially greater when the coffee grounds were incubated with both a β-1,3-galactanase and a mannanase. The increased yield is more than additive as compared to incubation with either enzyme alone indicating a synergistic effect. Without wishing to be bound by theory, the observed synergistic effect may be explained by galactomannans being incorporated into galactan-protein-melanoidin complexes in the coffee beans.

Therefore, in a preferred embodiment of the method of the invention, step b. further comprises addition of an enzyme having mannanase activity.

In another preferred embodiment, the roast and ground coffee beans have been partially extracted. Such coffee beans are also being referred to as spent coffee grounds.

The present invention also relates to a coffee extract which:

a. comprises at least 20% based on the total weight of soluble coffee solids of total galactose;
b. has a free galactose content of less than 50% by weight of the total galactose content;
c. has a weight ratio of total galactose to total arabinose of more than 3:1; and
d. is characterized in that at least 45% by weight of its carbohydrate fraction is oligosaccharides having a degree of polymerization of more than 5.

In a preferred embodiment, the coffee extract is further characterized in that at least 15% by weight of its carbohydrate fraction is oligosaccharides having a degree of polymerization of less than 55.

In another preferred embodiment, the coffee extract comprises arabinogalactan oligosaccharides having a degree of polymerization of above 2 and below 55 in an amount which is at least 15% based on total weight of soluble coffee solids.

DETAILED DESCRIPTION OF THE INVENTION

The term "β-1,3-galactanase" or "enzyme having β-1,3-galactanase activity" means an enzyme which specifically hydrolyses beta-1,3-galactan and beta-1,3-galactooligosaccharides. The enzyme may have primarily endo-β-1,3-galactanase activity (EC 3.2.1.181) or it may have exo activity (EC 3.2.1.145). For purposes of the present invention, β-1,3-galactanase activity is determined according to the procedures described in the Examples. In one aspect, a β-1,3-galactanases to be used in a method of the present invention has at least 20%, e.g., at least 40%, at least 50%, at least 60%, at least 70%, at least 80%, at least 90%, at least 95%, or at least 100% of the β-1,3-galactanase activity of the mature polypeptide of SEQ ID NO: 2. The β-1,3-galactanase activity may be quantified using the Reducing sugar assay (PAH-BAH assay) described in Example 7 with Smith degraded Gum Arabic or Acid treated Gum Arabic as substrate.

In the context of the present invention a "mannanase" is a beta-mannanase. It may be an enzyme defined according to the art as a mannan endo-1,4-beta-mannosidase (EC 3.2.1.78) which catalyses the hydrolysis of 1,4-β-D-mannosidic linkages in mannans, galactomannans and glucomannans, which enzyme has the alternative names 1,4-β-D-mannan mannanohydrolase; endo-1,4-β-mannanase; endo-β-1,4-mannase; β-mannanase B; β-1,4-mannan 4-mannanohydrolase; endo-β-mannanase; and β-D-mannanase. For purposes of the present invention, mannanase activity may be determined using the activity assay described by Staalbrand et al. (1993), Purification and characterization of two β-mannanases from *Trichoderma reesei*, J. Biotechnol., 29:229-42. In one aspect, a mannanase to be used in a method of the present invention has at least 20%, e.g., at least 40%, at least 50%, at least 60%, at least 70%, at least 80%, at least 90%, at least 95%, or at least 100% of the mannanase activity of the polypeptide of GENESEQP accession number AXU66990 shown herein as SEQ ID NO:15.

The term "mature polypeptide" means a polypeptide in its final form following translation and any post-translational modifications, such as N terminal processing, C terminal truncation, glycosylation, phosphorylation, etc. In one embodiment, the mature polypeptide of SEQ ID NO: 2 is amino acids 21 to 256 of SEQ ID NO: 2 based on the SignalP program (Nielsen et al., 1997, *Protein Engineering* 10: 1-6) predicting a signal peptide of 20 residues. In one embodiment, the mature polypeptide of SEQ ID NO: 4 is amino acids 26 to 258 of SEQ ID NO: 4 based on the SignalP program (Nielsen et al., 1997, *Protein Engineering* 10: 1-6) predicting a signal peptide of 25 residues. In one embodiment, the mature polypeptide of SEQ ID NO: 8 is amino acids 28 to 265 of SEQ ID NO: 8 based on the SignalP program (Nielsen et al., 1997, *Protein Engineering* 10: 1-6) predicting a signal peptide of 27 residues. In one embodiment, the mature polypeptide of SEQ ID NO: 10 is amino acids 21 to 448 of SEQ ID NO: 10 based on the SignalP program (Nielsen et al., 1997, *Protein Engineering* 10: 1-6) predicting a signal peptide of 20 residues. It is known in the art that a host cell may produce a mixture of two of more different mature polypeptides (i.e., with a different C terminal and/or N terminal amino acid) expressed by the same polynucleotide. It is also known in the art that different host cells process polypeptides differently, and thus, one host cell expressing a polynucleotide may produce a different mature polypeptide (e.g., having a different C terminal and/or N terminal amino acid) as compared to another host cell expressing the same polynucleotide.

The term "mature polypeptide coding sequence" means a polynucleotide that encodes a mature polypeptide.

Sequence identity: The relatedness between two amino acid sequences is described by the parameter "sequence identity". For purposes of the present invention, the sequence identity between two amino acid sequences is determined using the Needleman-Wunsch algorithm (Needleman and Wunsch, 1970, J. Mol. Biol. 48: 443-453) as implemented in the Needle program of the EMBOSS package (EMBOSS: The European Molecular Biology Open Software Suite, Rice et al., 2000, Trends Genet. 16: 276-277), preferably version 5.0.0 or later. The parameters used are gap open penalty of 10, gap extension penalty of 0.5, and the EBLOSUM62 (EMBOSS version of BLOSUM62) substitution matrix. The output of Needle labeled "longest identity" (obtained using the -nobrief option) is used as the percent identity and is calculated as follows:

(Identical Residues×100)/(Length of Alignment−
Total Number of Gaps in Alignment)

The present invention relates to a method for producing a coffee extract, comprising the steps:

a. providing roast and ground coffee beans;
b. adding to said coffee beans water and an enzyme having β-1,3-galactanase activity;
c. incubating to make an aqueous coffee extract; and
d. separating the coffee extract from the extracted coffee beans.

The method of the present invention can be applied to fresh roast and ground coffee beans or to roasted coffee grounds which have been previously extracted with water.

In a preferred embodiment, the roast and ground coffee beans have been partially extracted.

The method of the invention can be applied to ground coffee beans obtained by conventional soluble coffee processing. Therein, roast coffee is typically ground and (thermally) extracted with water in multiple stages. A two-stage execution is typical in the art, wherein the first stage comprises wetting the coffee grounds, recovery of flavour and extraction of the readily soluble components (such as caffeine, minerals and simple sugars). The second stage is typically a hydrolysis stage, where large coffee bio-polymers and bound components are broken down to smaller water-soluble ones. In the first stage, the roast coffee is typically extracted with water at or below 100° C. The grounds from this extraction, which may be referred to as "atmospheric grounds", are then extracted with superheated water at temperatures between 140° C. and 180° C. or even higher. The partially extracted grounds from the superheated extraction may be referred to as "super-heated grounds".

If the method of the invention is applied to partially extracted grounds, a first extraction may be carried out by adding the roast and ground coffee which may have an average particle size of about 900 micron to a jacketed stirred tank which contains water, wherein the solids to water ratio is about 1:5. The slurry is stirred, heated indirectly to a temperature of less than about 140° C., preferably in the range of about 85-90° C., and held at this temperature for about 30 minutes. The slurry is then discharged from the vessel and the subsequent grounds and extract separated using a filter. The partially extracted grounds are subjected to the method of the invention and the extract produced in the first extraction may be blended with the second extract produced using the method of the invention.

In the context of the present invention, partially extracted ground coffee beans or partially extracted coffee grounds means that the ground coffee beans have been subjected to at least one extraction. Such partially extracted ground coffee beans may also be referred to as spent coffee grounds.

The method of the invention may, in general, be applied to roast and ground coffee comprising roasted beans which were ground to an average particle size of between about 0.3 to about 5 mm, preferably between about 0.4 to about 0.9 mm.

In addition, a flavour management pre-treatment step can be added to the method of the invention to recover the aroma compounds or aromatic constituents of the coffee prior to the extraction and/or hydrolysis stages. Useful processes include, but are not limited to, those described in EP 0 489 401. A practical execution includes wetting roast and ground coffee with water in a vessel in a ratio of about 1:0.5 by weight. Vacuum is applied to the vessel (e.g., about 150 mbar) and then low pressure steam is applied to the bed of wetted grounds for up to about 4 to 8 minutes to evaporate aroma compounds from the roast and ground coffee. Volatile compounds drawn off are condensed, for example at about 5° C. and retained to be added back to extracts or extracted solids.

The method of the invention can be practiced on roast coffee which has been steamed-purged at low pressure to extract volatile flavour components, as described above.

The method of the invention may be applied to any type of coffee grounds with hydrolysable matter known to those skilled in the art, such as de-oiled coffee grounds, decaffeinated coffee grounds, wet-milled coffee grounds, etc.

The enzymatic treatment of the roast and ground coffee beans is to be performed at a temperature where the enzymes are active and for sufficiently long time to permit enzyme reaction.

In one possible batch mode of operation, after the enzymatic reaction is essentially completed, the mixture is subjected to a gross separation, for example centrifugation or belt filtration, which removes most of the insoluble solids. The separated extract, still containing fine particulates, oil and enzyme protein, is recirculated through a cross-flow membrane device, which removes all insolubles and can also remove enzyme. Most or all of the enzyme remains in the membrane retentate and may be recycled to the reaction.

In one possible mode of operation, semi-permeable membrane permeate is constantly withdrawn during the enzyme reaction, i.e. a portion of the reaction mixture is continuously circulated through the cross-flow semi-permeable membrane separation cell. The process can be operated in a semi-continuous mode, wherein permeate is withdrawn until the volume in the reaction vessel diminishes to the point where its viscosity or the pressure drop becomes high. At this point, some retentate is purged and fresh coffee slurry fed and some fresh enzyme added. The purged retentate can be discarded or can be washed to recover the enzyme which is then re-used. The enzyme in the remaining (non-purged) retentate is retained and re-used.

Alternatively, fresh feed slurry may be continuously added to the feed tank together with some enzyme with a purge drawn from the recycle stream of equal volume.

In any event, running the process in a semi-continuous or continuous mode of operation permits permeation of solubilized components out of the reaction zone before they can be further broken down.

If the method of the invention is used for treating grounds from roast and ground coffee which has been previously extracted with water and/or thermally hydrolysed, the extract obtained from the method of this invention can be combined with the extracts obtained beforehand.

Where atmospheric grounds are used as the feed to the method of the invention, the extract produced may be combined with the extract obtained during the atmospheric extraction stage. The extracts are combined based on the ratio of extracted roasted yields from each stage. The combined extract is then concentrated, aromatised and dried as is conventional in the art.

The coffee extract can be dehydrated, such as a soluble coffee or dry mix composition, or it can be a ready-to-drink coffee product, a liquid mix composition, a frozen composition or a liquid concentrate composition. The coffee extract of the invention can also be used in non-beverage applications, such as instant desserts or confectionery products etc.

The processes to make those coffee compositions from soluble coffee extracts are known to a person skilled in the art.

In the method of the invention, water and enzyme is added to the coffee beans which may have been partially extracted.

Water may, e.g., be added so that the final concentration of dry matter is between 2%30% (w/w), preferably between 5%-20% (w/w), such as about 10% (w/w).

The enzyme having β-1,3-galactanase activity may be added at a concentration of at least 0.001 g enzyme protein/kg coffee beans, preferably at least 0.005 g enzyme protein/kg coffee beans, such as at a concentration of 0.001-0.5 g enzyme protein/kg coffee beans, preferably 0.005-0.2 g enzyme protein/kg coffee beans.

The enzyme having β-1,3-galactanase activity is preferably added as an enzymatic preparation characterized in that at least 5%, preferably at least 10% or at least 20%, of the total protein in the preparation is an enzyme having β-1,3-galactanase activity as its predominant enzymatic activity.

In one embodiment, the enzyme having β-1,3-galactanase activity has an activity at 60° C. which is at least 50%, preferably at least 60% or at least 70%, of its activity at 40° C. The activity at different temperatures may be determined as described in Example 11.

In one embodiment, the enzyme having β-1,3-galactanase activity has a relative activity for degrading Smith degraded Gum Arabic which is at least 10-fold higher than its relative activity for degrading Gum Arabic. The relative activity for degrading these substrates having a different degree of branching may be determined as described in Examples 6-7.

In one embodiment, the enzyme having β-1,3-galactanase activity is a β-1,3-galactanase, preferably an endo-β-1,3-galactanase (EC 3.2.1.181) or an exo-β-1,3-galactanase (EC 3.2.1.145). In one embodiment, the enzyme having β-1,3-galactanase activity is an endo-β-1,3-galactanase (EC 3.2.1.181). In another embodiment, the enzyme having β-1,3-galactanase activity is an exo-β-1,3-galactanase (EC 3.2.1.145).

In one embodiment, the enzyme having β-1,3-galactanase activity has primarily endo-β-1,3-galactanase activity.

In one embodiment, the enzyme having β-1,3-galactanase activity is a β-1,3-galactanase of the GH16 family.

In one embodiment, the enzyme having β-1,3-galactanase activity has an amino acid sequence which has at least 60% identity to the mature sequence of any of SEQ ID NOs: 2, 4 or 8. Preferably, the enzyme having β-1,3-galactanase activity has an amino acid sequence which has at least 65%, e.g., at least 70%, at least 75%, at least 80%, at least 85%, at least 90%, at least 91%, at least 92%, at least 93%, at least 94%, at least 95%, at least 96%, at least 97%, at least 98%, at least 99%, or 100%, identity to the mature sequence of any of SEQ ID NOs: 2, 4 or 8. In another embodiment, the enzyme having β-1,3-galactanase activity differ by up to 10 amino acids, e.g., 1, 2, 3, 4, 5, 6, 7, 8, 9, or 10 amino acids, from the mature polypeptide of any of SEQ ID NOs: 2, 4 or 8.

In one embodiment, the enzyme having β-1,3-galactanase activity has an amino acid sequence which has at least 60% identity to the mature sequence of SEQ ID NO: 2. Preferably, the enzyme having β-1,3-galactanase activity has an amino acid sequence which has at least 65%, e.g., at least 70%, at least 75%, at least 80%, at least 85%, at least 90%, at least 91%, at least 92%, at least 93%, at least 94%, at least 95%, at least 96%, at least 97%, at least 98%, at least 99%, or 100%, identity to the mature sequence of SEQ ID NO: 2. In another embodiment, the enzyme having β-1,3-galactanase activity differ by up to 10 amino acids, e.g., 1, 2, 3, 4, 5, 6, 7, 8, 9, or 10 amino acids, from the mature polypeptide of SEQ ID NO: 2.

In one embodiment, the enzyme having β-1,3-galactanase activity has an amino acid sequence which has at least 60% identity to the mature sequence of SEQ ID NO: 4. Preferably, the enzyme having β-1,3-galactanase activity has an amino acid sequence which has at least 65%, e.g., at least 70%, at least 75%, at least 80%, at least 85%, at least 90%, at least 91%, at least 92%, at least 93%, at least 94%, at least 95%, at least 96%, at least 97%, at least 98%, at least 99%, or 100%, identity to the mature sequence of SEQ ID NO: 4. In another embodiment, the enzyme having β-1,3-galactanase activity differ by up to 10 amino acids, e.g., 1, 2, 3, 4, 5, 6, 7, 8, 9, or 10 amino acids, from the mature polypeptide of SEQ ID NO: 4.

In one embodiment, the enzyme having β-1,3-galactanase activity has an amino acid sequence which has at least 60% identity to the mature sequence of SEQ ID NO: 8. Preferably, the enzyme having β-1,3-galactanase activity has an amino acid sequence which has at least 65%, e.g., at least 70%, at least 75%, at least 80%, at least 85%, at least 90%, at least 91%, at least 92%, at least 93%, at least 94%, at least 95%, at least 96%, at least 97%, at least 98%, at least 99%, or 100%, identity to the mature sequence of SEQ ID NO: 8. In another embodiment, the enzyme having β-1,3-galactanase activity differ by up to 10 amino acids, e.g., 1, 2, 3, 4, 5, 6, 7, 8, 9, or 10 amino acids, from the mature polypeptide of SEQ ID NO: 8.

In one embodiment, the enzyme having β-1,3-galactanase activity is a β-1,3-galactanase of the GH43 family.

In one embodiment, the enzyme having β-1,3-galactanase activity has an amino acid sequence which has at least 60% identity to the mature sequence of SEQ ID NO: 10. Preferably, the enzyme having β-1,3-galactanase activity has an amino acid sequence which has at least 65%, e.g., at least 70%, at least 75%, at least 80%, at least 85%, at least 90%, at least 91%, at least 92%, at least 93%, at least 94%, at least 95%, at least 96%, at least 97%, at least 98%, at least 99%, or 100%, identity to the mature sequence of SEQ ID NO: 10. In another embodiment, the enzyme having β-1,3-galactanase activity differ by up to 10 amino acids, e.g., 1, 2, 3, 4, 5, 6, 7, 8, 9, or 10 amino acids, from the mature polypeptide of SEQ ID NO: 10.

A β-1,3-galactanase to be used in the method of the present invention may be obtained from microorganisms of any genus. For purposes of the present invention, the term "obtained from" as used herein in connection with a given source shall mean that the polypeptide encoded by a polynucleotide is produced by the source or by a strain in which the polynucleotide from the source has been inserted. In one embodiment, the β-1,3-galactanase obtained from a given source is secreted extracellularly.

The β-1,3-galactanase may be a bacterial β-1,3-galactanase. For example, the β-1,3-galactanase may be a Gram-positive bacterial β-1,3-galactanase such as a *Bacillus, Clostridium, Enterococcus, Geobacillus, Lactobacillus, Lactococcus, Oceanobacillus, Staphylococcus, Streptococcus,* or *Streptomyces* β-1,3-galactanase, or a Gram-negative bacterial β-1,3-galactanase such as a *Campylobacter, E. coli, Flavobacterium, Fusobacterium, Helicobacter, Ilyobacter, Neisseria, Pseudomonas, Salmonella,* or *Ureaplasma* β-1,3-galactanase.

The β-1,3-galactanase may be a fungal β-1,3-galactanase. For example, the β-1,3-galactanase may be a yeast β-1,3-galactanase such as a *Candida, Kluyveromyces, Pichia, Saccharomyces, Schizosaccharomyces,* or *Yarrowia* β-1,3-galactanase; or a filamentous fungal β-1,3-galactanase such as an *Acremonium, Agaricus, Alternaria, Aspergillus, Aureobasidium, Botryosphaeria, Ceriporiopsis, Chaetomidium, Chrysosporium, Claviceps, Cochliobolus, Coprinopsis, Coptotermes, Corynascus, Cryphonectria, Cryptococcus, Diplodia, Exidia, Filibasidium, Fusarium, Gibberella, Holomastigotoides, Humicola, Irpex, Lentinula, Leptospaeria, Magnaporthe, Melanocarpus, Meripilus, Mucor, Myceliophthora, Neocallimastix, Neurospora, Paecilomyces, Penicillium, Phanerochaete, Piromyces, Poitrasia, Pseudoplectania, Pseudotrichonympha, Rhizomucor, Schizophyllum, Scytalidium, Talaromyces, Thermoascus, Thielavia, Tolypocladium, Trichoderma, Trichophaea, Verticillium, Volvariella,* or *Xylaria* β-1,3-galactanase.

In one embodiment, the β-1,3-galactanase is obtained from *Auricularia*, preferably from *Auricularia delicata*.

In one embodiment, the β-1,3-galactanase is obtained from *Magnaporthe*, preferably from *Magnaporthe oryzae*.

In one embodiment, the β-1,3-galactanase is obtained from *Neurospora*, preferably from *Neurospora crassa*.

In one embodiment, the β-1,3-galactanase is obtained from *Irpex*, preferably from *Irpex lacteus*.

It will be understood that for the aforementioned species, the invention encompasses both the perfect and imperfect states, and other taxonomic equivalents, e.g., anamorphs, regardless of the species name by which they are known. Those skilled in the art will readily recognize the identity of appropriate equivalents.

Strains of these species are readily accessible to the public in a number of culture collections, such as the American Type Culture Collection (ATCC), Deutsche Sammlung von Mikroorganismen and Zellkulturen GmbH (DSMZ), Centraalbureau Voor Schimmelcultures (CBS), and Agricultural Research Service Patent Culture Collection, Northern Regional Research Center (NRRL).

The β-1,3-galactanase may be identified and obtained from other sources including microorganisms isolated from nature (e.g., soil, composts, water, etc.) or DNA samples obtained directly from natural materials (e.g., soil, composts, water, etc.) using appropriate probes. Techniques for isolating microorganisms and DNA directly from natural habitats are well known in the art. A polynucleotide encoding the β-1,3-galactanase may then be obtained by similarly screening a genomic DNA or cDNA library of another microorganism or mixed DNA sample. Once a polynucleotide encoding a β-1,3-galactanase has been detected with the probe(s), the polynucleotide can be isolated or cloned by utilizing techniques that are known to those of ordinary skill in the art (see, e.g., Sambrook et al., 1989, *Molecular Cloning, A Laboratory Manual*, 2nd edition, Cold Spring Harbor, New York).

In an embodiment of the method of the invention, step b. further comprises addition of an enzyme having mannanase activity.

A mannanase to be used in the method of the present invention may be obtained from microorganisms of any genus. Mannanases have been identified, e.g., in several *Bacillus* organisms. For example, Talbot et al. (1990), Appl. Environ. Microbiol., Vol. 56, No. 11, pp. 3505-3510, describes a beta-mannanase derived from *Bacillus stearothermophilus* having an optimum pH of 5.5-7.5. Mendoza et al. (1994), World J. Microbiol. Biotech., Vol. 10, No. 5, pp. 551-555, describes a beta-mannanase derived from *Bacillus subtilis* having an optimum activity at pH 5.0 and 55° C. JP-03047076 discloses a beta-mannanase derived from *Bacillus* sp., having an optimum pH of 8-10. JP-63056289 describes the production of an alkaline, thermostable beta-mannanase. JP-08051975 discloses alkaline beta-mannanases from alkalophilic *Bacillus* sp. AM-001. A purified mannanase from *Bacillus amyloliquefaciens* is disclosed in WO 97/11164. WO 94/25576 discloses an enzyme from *Aspergillus aculeatus*, CBS 101.43, exhibiting mannanase activity and WO 93/24622 discloses a mannanase isolated from *Trichoderma reesei*.

A suitable commercial mannanase preparation is Mannaway® produced by Novozymes A/S.

In one embodiment, the enzyme having mannanase activity has an amino acid sequence which has at least 60% identity to SEQ ID NO: 15. Preferably, the enzyme having mannanase activity has an amino acid sequence which has at least 65%, e.g., at least 70%, at least 75%, at least 80%, at least 85%, at least 90%, at least 91%, at least 92%, at least 93%, at least 94%, at least 95%, at least 96%, at least 97%, at least 98%, at least 99%, or 100%, identity to SEQ ID NO: 15. In another embodiment, the enzyme having mannanase activity differ by up to 10 amino acids, e.g., 1, 2, 3, 4, 5, 6, 7, 8, 9, or 10 amino acids, from the polypeptide of SEQ ID NO: 15.

In one embodiment, the mannanase is obtained from a strain of the genus *Bacillus*.

In one embodiment, the mannanase is the mannanase having the amino acid sequence GEN ESEQP:AXU66990 disclosed in WO2010000858.

In one embodiment of the method of the invention, the enzyme having β-1,3-galactanase activity and the enzyme having mannanase activity act synergistically to increase the amount of solubilised coffee solids.

In the method of the invention, after the water and the enzyme has been added to the roast and ground coffee beans, the composition comprising the coffee beans, the water and the enzyme is incubated to make an aqueous coffee extract.

The incubation is to be performed at a temperature where the enzymes are active, typically in the range of about 25° C. to about 90° C., preferably about 35° C. to about 70° C. for about 1 to about 24 hours, preferably about 4 to about 24 hours to permit enzyme reaction.

After the incubation, the coffee extract is separated from the extracted coffee beans by any means known in the art.

In one embodiment, the coffee extract obtained by the method of the invention comprises at least 20% based on the total weight of soluble coffee solids of total galactose. Preferably, the coffee extract comprises at least 25% based on the total weight of soluble coffee solids of total galactose.

Total galactose in the coffee extract in the context of the present invention means solubilized free galactose plus galactose bound in solubilized oligosaccharides.

In one embodiment, the free galactose content in the coffee extract obtained by the method of the invention is less than 50% by weight of the total galactose content. Preferably, the free galactose content is less than 40% by weight, preferably less than 30% or less than 25% by weight, of the total galactose content. In one embodiment, the free galactose content is less than 20% by weight, preferably less than 15% or less than 10% by weight, of the total galactose content.

In one embodiment, the coffee extract obtained by the method of the invention has a weight ratio of total galactose to total arabinose of more than 3:1, preferably more than 4:1 or more than 5:1.

Total arabinose in the coffee extract in the context of the present invention means solubilized free arabinose plus arabinose bound in solubilized oligosaccharides.

In one embodiment, the coffee extract obtained by the method of the invention is characterized in that at least 45% by weight of its carbohydrate fraction is oligosaccharides having a degree of polymerization of more than 5. Preferably, at least 50% by weight, e.g., at least 55% or at least 60% by weight, of its carbohydrate fraction is oligosaccharides having a degree of polymerization of more than 5.

In one embodiment, the coffee extract obtained by the method of the invention is characterized in that at least 15% by weight of its carbohydrate fraction is oligosaccharides having a degree of polymerization of less than 55. Preferably, at least 15% by weight of its carbohydrate fraction is oligosaccharides having a degree of polymerization of less than 45, e.g., less than 35 or less than 25.

In one embodiment, the coffee extract obtained by the method of the invention comprises arabinogalactan oligosaccharides having a degree of polymerization of above 2 and below 55 in an amount which is at least 15% based on total weight of soluble coffee solids.

In another aspect, the present invention relates to a coffee extract which:
  a. comprises at least 20% based on the total weight of soluble coffee solids of total galactose;
  b. has a free galactose content of less than 50% by weight of the total galactose content;
  c. has a weight ratio of total galactose to total arabinose of more than 3:1; and
  d. is characterized in that at least 45% by weight of its carbohydrate fraction is oligosaccharides having a degree of polymerization of more than 5.

In one embodiment, the coffee extract comprises at least 20% based on the total weight of soluble coffee solids of total galactose. Preferably, the coffee extract comprises at least 25% based on the total weight of soluble coffee solids of total galactose.

In one embodiment, the free galactose content in the coffee extract is less than 40% by weight, preferably less than 30% or less than 25% by weight, of the total galactose content. In one embodiment, the free galactose content is less than 20% by weight, preferably less than 15% or less than 10% by weight, of the total galactose content.

In one embodiment, the coffee extract has a weight ratio of total galactose to total arabinose of more than 4:1 or more than 5:1.

In one embodiment, the coffee extract is characterized in that at least 50% by weight, e.g., at least 55% or at least 60% by weight, of its carbohydrate fraction is oligosaccharides having a degree of polymerization of more than 5.

In a preferred embodiment, the coffee extract is further characterized in that at least 15% by weight of its carbohydrate fraction is oligosaccharides having a degree of polymerization of less than 55. Preferably, at least 15% by weight of its carbohydrate fraction is oligosaccharides having a degree of polymerization of less than 45, e.g., less than 35 or less than 25.

In another preferred embodiment, the coffee extract comprises arabinogalactan oligosaccharides having a degree of polymerization of above 2 and below 55 in an amount which is at least 15% based on total weight of soluble coffee solids.

EXAMPLES

Materials and Methods

In the examples below the following galactanase enzymes were used:

| SEQ ID NO: | Example | Description | Origin | GH |
|---|---|---|---|---|
| 2 | Example 1 | Endo-β-1,3-galactanase | Auricularia delicata | GH16 |
| 4 | Example 2 | Endo-β-1,3-galactanase | Magnaporthe oryzae | GH16 |
| 8 | Example 3 | Endo-β-1,3-galactanase | Neurospora crassa | GH16 |
| 10 | Example 4 | Exo-β-1,3-galactanase | Irpex lacteus | GH43 |
| 12 | Example 5 | Endo-β-1,4-galactanase | Ignisphaera aggregans | GH53 |

The mannanase enzyme used in the examples is Mannaway® 25L.

Materials

Chemicals used as buffers and substrates were commercial products of at least reagent grade.

Media and Solutions

YP+2% glucose medium was composed of 1% yeast extract, 2% peptone and 2% glucose.

PDA agar plates were composed of potato infusion (potato infusion was made by boiling 300 g of sliced (washed but unpeeled) potatoes in water for 30 minutes and then decanting or straining the broth through cheesecloth. Distilled water was then added until the total volume of the suspension was one liter, followed by 20 g of dextrose and 20 g of agar powder. The medium was sterilized by autoclaving at 15 psi for 15 minutes (Bacteriological Analytical Manual, 8th Edition, Revision A, 1998).

LB plates were composed of 10 g of Bacto-Tryptone, 5 g of yeast extract, 10 g of sodium chloride, 15 g of Bacto-agar, and deionized water to 1 liter. The medium was sterilized by autoclaving at 15 psi for 15 minutes (Bacteriological Analytical Manual, 8th Edition, Revision A, 1998).

COVE sucrose plates were composed of 342 g Sucrose (Sigma S-9378), 20 g Agar powder, 20 ml Cove salt solution (26 g $MgSO_4 \cdot 7H_2O$, 26 g KCL, 26 g $KH_2PO_4$, 50 ml Cove trace metal solution) and deionized water to 1 liter), and deionized water to 1 liter). The medium was sterilized by autoclaving at 15 psi for 15 minutes (Bacteriological Analytical Manual, 8th Edition, Revision A, 1998). The medium was cooled to 60° C. and added 10 mM acetamide, 15 mM CsCl, Triton X-100 (50 µl/500 ml)).

Cove trace metal solution was composed of 0.04 g $Na_2B_4O_7 \cdot 10H_2O$, 0.4 g $CuSO_4 \cdot 5H_2O$, 1.2 g $FeSO_4 \cdot 7H_2O$, 0.7 g $MnSO_4 \cdot H_2O$, 0.8 g $Na_2MoO_4 \cdot 2H_2O$, 10 g $ZnSO_4 \cdot 7H_2O$, and deionized water to 1 liter.

Example 1

Cloning, Expression and Purification of the Auricularia delicata Endo-β-1,3-Galactanase (GALACTANASE1)

The assembly of the genome of Auricularia delicata SS-5 (DOE Joint Genome Institute, Walnut Creek, CA 94598, USA) were retrieved from NCBI, Bethesda MD, USA, together with corresponding gene models and used as a starting point for detecting GH16 homologues in the genome. More precise gene models were constructed manually using multiple known GH16 protein sequences as a guide.

Construction of an Aspergillus oryzae Expression Vector Containing Auricularia delicata cDNA Sequence Encoding a Family GH16 Polypeptide Having Endo-β-1,3-Galactanase Activity Based on the nucleotide sequence of the Auricularia delicata SS-5 genome sequence (DOE Joint Genome Institute, Walnut Creek, CA 94598, USA), a synthetic gene P24GUG (SEQ ID NO: 1) was obtained from GeneArt (Invitrogen, Carlsbad, CA, USA) encoding the cDNA of the Auricularia delicata endo-beta-1,3-galactanase with additional BamHI and XhoI restriction sites to facilitate cloning into an expression vector.

The GeneArt construct containing P24GUG was treated with BamHI and XhoI restriction enzymes and the reaction products were isolated by 1.0% agarose gel electrophoresis using 40 mM Tris base, 20 mM sodium acetate, 1 mM disodium EDTA (TAE) buffer where a 780 bp product band was excised from the gel and purified using an illustra GFX® PCR DNA and Gel Band Purification Kit (GE Healthcare Life Sciences, Brondby, Denmark) according to the manufacturer's instructions. The fragment was then cloned by ligation into Bam HI and Xho I digested pDau109 using T4 DNA ligase (Roche Diagnostics A/S, Hvidovre, Denmark) according to the manufacturer's instructions resulting in plasmid pP24GUG. Cloning of the P24GUG gene into Bam HI-Xho I digested pDau109 resulted in the transcription of the *Auricularia* delicata P24GUG gene under the control of a NA2-tpi double promoter. NA2-tpi is a modified promoter from the gene encoding the *Aspergillus niger* neutral alpha-amylase in which the untranslated leader has been replaced by an untranslated leader from the gene encoding the *Aspergillus nidulans* triose phosphate isomerase.

The ligated plasmid pP24GUG was transformed into One Shot® TOP10F' Chemically Competent *E. coli* cells (Invitrogen, Carlsbad, CA, USA) according to the manufacturer's protocol and plated onto LB plates supplemented with 0.1 mg of ampicillin per ml. After incubating at 37° C. overnight, colonies were seen growing under selection on the LB ampicillin plates. Two colonies transformed with the P24GUG GH16 construct were cultivated in LB medium supplemented with 0.1 mg of ampicillin per ml and plasmid was isolated with a QIAprep Spin Miniprep Kit (QIAGEN Inc., Valencia, CA, USA) according to the manufacturer's protocol.

Isolated plasmids were sequenced with vector primers and P24GUG gene specific primers in order to determine a representative plasmid expression clone that was free of errors.

Characterization of the *Auricularia delicata* cDNA Sequence Encoding a GH16 Polypeptide Having endo-β-1,3-galactanase Activity DNA sequencing of the *Auricularia delicata* P24GUG GH16 cDNA clone was performed with an Applied Biosystems Model 3700 Automated DNA Sequencer using version 3.1 BIG-DYE™ terminator chemistry (Applied Biosystems, Inc., Foster City, CA, USA) and primer walking strategy. Nucleotide sequence data were scrutinized for quality and all sequences were compared to each other with assistance of PHRED/PHRAP software (University of Washington, Seattle, WA, USA).

The nucleotide sequence and deduced amino acid sequence of the *Auricularia delicata* P24GUG gene is shown in SEQ ID NO: 1 and SEQ ID NO: 2, respectively. The coding sequence is 771 bp including the stop codon. The encoded predicted protein is 256 amino acids. Using the SignalP program (Nielsen et al., 1997, *Protein Engineering* 10: 1-6), a signal peptide of 20 residues was predicted. The predicted mature protein contains 236 amino acids with a predicted molecular mass of 26 kDa and an isoelectric pH of 7.3.

Expression of the *Auricularia delicata* GH16 Endo-β-1,3-Galactanase (GALACTANASE1)

The expression plasmid pP24GUG was transformed into *Aspergillus oryzae* MT3568. *Aspergillus oryzae* MT3568 is an AMDS (acetamidase) disrupted derivative of JaL355 (WO 02/40694) in which pyrG auxotrophy was restored in the process of knocking out the *Aspergillus oryzae* acetamidase (AMDS) gene. MT3568 protoplasts are prepared according to the method of European Patent No. 0238023, pages 14-15, which are incorporated herein by reference.

Transformants were purified on COVE sucrose selection plates through single conidia prior to sporulating them on PDA plates. Production of the *Auricularia delicata* GH16 polypeptide by the transformants was analyzed from culture supernatants of 1 ml 96 deep well stationary cultivations at 30° C. in YP+2% glucose medium. Expression was verified on an E-Page 8% SDS-PAGE 48 well gel (Invitrogen, Carlsbad, CA, USA) by Coomassie staining. One transformant was selected for further work and designated *Aspergillus oryzae* 99.1.

For larger scale production, *Aspergillus oryzae* 99.1 spores were spread onto a PDA plate and incubated for five days at 37° C. The confluent spore plate was washed twice with 5 ml of 0.01% TWEEN® 20 to maximize the number of spores collected. The spore suspension was then used to inoculate fifteen 500 ml flasks containing 150 ml of Dap-4C medium (WO 2012/103350). The culture was incubated at 30° C. with constant shaking at 100 rpm. At day four post-inoculation, the culture broth was collected by filtration through a bottle top MF75 Supor MachV 0.2 µm PES filter (Thermo Fisher Scientific, Roskilde, Denmark). Fresh culture broth from this transformant produced a band of GH16 protein of approximately 26 kDa. The identity of the band as the *Auricularia delicata* GH16 polypeptide was verified by peptide sequencing.

Purification of the *Auricularia delicata* Endo-β-1,3-Galactanase (GALACTANASE1)

The harvested cell culture broth of *Auricularia delicata* GALACTANASE1 was supplemented with ammonium sulphate to a final concentration of 2 M and pH was adjusted to 7.5. The sample was then loaded on a hydrophobic column (packed bed of butyl Toyo pearl; gradient: 0-100% B in 10 column volumes; buffer A: 50 mM Mes and 2 M ammonium sulphate; buffer B: 50 mM Mes). SDS-PAGE (reducing conditions) confirmed that the galactanase was not eluted through the column in the flow-through or wash fraction. Based on the SDS-PAGE, fractions containing proteins of the expected Mw of 27.7 kDa (fractions 30-50) were pooled, concentrated and buffer-exchanged into 20 mM sodium acetate buffer pH 6.5 by centrifugation in viva spin column 3 kDa MWCO membrane (3000×g spin centrifugation).

Example 2

Cloning, Expression and Purification of the *Magnaporthe oryzae* Endo-β-1,3-Galactanase (GALACTANASE2)

Construction of an *Aspergillus oryzae* Expression Vector Containing *Magnaporthe oryzae* cDNA Sequence Encoding a Family GH16 Polypeptide Having Endo-β-1,3-Galactanase Activity A preliminary assembly of the genome of *Magnaporthe oryzae* 70-15 (DOE Joint Genome Institute, Walnut Creek, CA 94598, USA) was analyzed using GeneMark v2.3c (Georgia Tech's Center for Bioinformatics and Computational Genomics, Atlanta, Georgia, USA). Gene models constructed by the software were used as a starting point for detecting GH16 homologues in the genome. More precise gene models were constructed manually using multiple known GH16 protein sequences as a guide. One such obtained sequence was identical to Swissprot entry A4QYM3 annotated as a GH16 putative uncharacterized protein.

Based on the nucleotide sequence of the *Magnaporthe oryzae* 70-15 genome sequence (Wellcome Trust Genome Campus, Cambridge, United Kingdom), a synthetic gene P24HNK (SEQ ID NO: 3) was obtained from GeneArt (Invitrogen, Carlsbad, CA, USA) encoding the cDNA of the *Magnaporthe oryzae* endo-beta-1,3-galactanase with additional BamHI and XhoI restriction sites to facilitate cloning into an expression vector.

The GeneArt construct containing P24HNK was treated with BamHI and XhoI restriction enzymes and the reaction products were isolated by 1.0% agarose gel electrophoresis using 40 mM Tris base, 20 mM sodium acetate, 1 mM disodium EDTA (TAE) buffer where a 790 bp product band was excised from the gel and purified using an illustra GFX® PCR DNA and Gel Band Purification Kit (GE Healthcare Life Sciences, Brondby, Denmark) according to the manufacturer's instructions. The fragment was then cloned by ligation into Bam HI and Xho I digested pDau109 using T4 DNA ligase (Roche Diagnostics A/S, Hvidovre, Denmark) according to the manufacturer's instructions resulting in plasmid pP24HNK. Cloning of the P24HNK gene into Bam HI-Xho I digested pDau109 resulted in the transcription of the *Magnaporthe oryzae* P24HNK gene under the control of a NA2-tpi double promoter. NA2-tpi is a modified promoter from the gene encoding the *Aspergillus niger* neutral alpha-amylase in which the untranslated leader has been replaced by an untranslated leader from the gene encoding the *Aspergillus nidulans* triose phosphate isomerase.

The ligated plasmid pP24HNK was transformed into One Shot® TOP10F' Chemically Competent *E. coli* cells (Invitrogen, Carlsbad, CA, USA) according to the manufacturer's protocol and plated onto LB plates supplemented with 0.1 mg of ampicillin per ml. After incubating at 37° C. overnight, colonies were seen growing under selection on the LB ampicillin plates. Two colonies transformed with the P24HNK GH16 construct were cultivated in LB medium supplemented with 0.1 mg of ampicillin per ml and plasmid was isolated with a QIAprep Spin Miniprep Kit (QIAGEN Inc., Valencia, CA, USA) according to the manufacturer's protocol.

Isolated plasmids were sequenced with vector primers and P24HNK gene specific primers in order to determine a representative plasmid expression clone that was free of errors.

Characterization of the *Magnaporthe oryzae* cDNA Sequence Encoding a P24HNK GH16 Polypeptide Having Endo-β-1,3-Galactanase Activity DNA sequencing of the *Magnaporthe oryzae* P24HNK GH16 cDNA clone was performed with an Applied Biosystems Model 3700 Automated DNA Sequencer using version 3.1 BIG-DYE™ terminator chemistry (Applied Biosystems, Inc., Foster City, CA, USA) and primer walking strategy. Nucleotide sequence data were scrutinized for quality and all sequences were compared to each other with assistance of PHRED/PHRAP software (University of Washington, Seattle, WA, USA).

The nucleotide sequence and deduced amino acid sequence of the *Magnaporthe oryzae* P24HNK gene is shown in SEQ ID NO: 3 and SEQ ID NO: 4, respectively. The coding sequence is 777 bp including the stop codon. The encoded predicted protein is 258 amino acids. Using the SignalP program (Nielsen et al., 1997, *Protein Engineering* 10: 1-6), a signal peptide of 25 residues was predicted. The predicted mature protein contains 233 amino acids with a predicted molecular mass of 26 kDa and an isoelectric pH of 4.9.

Expression of the *Magnaporthe oryzae* GH16 Endo-β-1,3-Galactanase GALACTANASE2

The expression plasmid pP24HNK was transformed into *Aspergillus oryzae* MT3568. *Aspergillus oryzae* MT3568 is an AMDS (acetamidase) disrupted derivative of JaL355 (WO 02/40694) in which pyrG auxotrophy was restored in the process of knocking out the *Aspergillus oryzae* acetamidase (AMDS) gene. MT3568 protoplasts are prepared according to the method of European Patent No. 0238023, pages 14-15, which are incorporated herein by reference.

Transformants were purified on COVE sucrose selection plates through single conidia prior to sporulating them on PDA plates. Production of the *Magnaporthe oryzae* GH16 polypeptide by the transformants was analyzed from culture supernatants of 1 ml 96 deep well stationary cultivations at 30° C. in YP+2% glucose medium. Expression was verified on an E-Page 8% SDS-PAGE 48 well gel (Invitrogen, Carlsbad, CA, USA) by Coomassie staining. One transformant was selected for further work and designated *Aspergillus oryzae* 100.3.

For larger scale production, *Aspergillus oryzae* 100.3 spores were spread onto a PDA plate and incubated for five days at 37° C. The confluent spore plate was washed twice with 5 ml of 0.01% TWEEN® 20 to maximize the number of spores collected. The spore suspension was then used to inoculate fifteen 500 ml flasks containing 150 ml of Dap-4C medium (WO 2012/103350). The culture was incubated at 30° C. with constant shaking at 100 rpm. At day four post-inoculation, the culture broth was collected by filtration through a bottle top MF75 Supor MachV 0.2 μm PES filter (Thermo Fisher Scientific, Roskilde, Denmark). Fresh culture broth from this transformant produced a band of GH16 protein of approximately 26 kDa. The identity of the band as the *Magnaporthe oryzae* GH16 polypeptide was verified by peptide sequencing.

Purification of the *Magnaporthe oryzae* Endo-β-1,3-Galactanase (GALACTANASE2)

The harvested cell culture broth of *Magnaporthe oryzae* was supplemented with 1.5 M ammonium sulphate to a final concentration of 1.5 M and pH was adjusted to 7. The sample was then loaded on a hydrophobic column (packed bed of butyl Toyo pearl; gradient: 0-100% B in 10 column volumes; buffer A: 50 mM Mes and 1.5 M ammonium sulphate; buffer B: 50 mM Mes). SDS-PAGE (reducing conditions) confirmed that the galactanase was not eluted through the column in the flow-through or wash fraction. Based on the SDS-PAGE, fractions containing proteins of the expected Mw of 28.5 kDa (fractions 33-46) were pooled, concentrated and buffer-exchanged into 20 mM sodium acetate buffer pH 6.5 by centrifugation in viva spin column 3 kDa MWCO membrane (3000×g spin centrifugation).

Example 3

Cloning, Expression and Purification of the *Neurospora crassa* Endo-β-1,3-Galactanase (GALACTANASE3)

*Neurospora crassa* Strain FGSC987 Genomic DNA Extraction

To generate genomic DNA for PCR amplification, *Neurospora crassa* Strain FGSC987 (ATCC 24698, LGC Standards AB, Boras, Sweden) was propagated on PDA agar plates by growing at 26° C. for 7 days. Spores harvested from the PDA plates were used to inoculate 25 ml of YP+2% glucose medium in a baffled shake flask and incubated at 26° C. for 72 hours with agitation at 85 rpm.

Genomic DNA was isolated according to a modified DNeasy Plant Maxi kit protocol (Qiagen Danmark, Copenhagen, Denmark). The fungal material from the above culture was harvested by centrifugation at 14,000×g for 2 minutes. The supernatant was removed and the 0.5 g of the pellet was frozen in liquid nitrogen with quartz sand and grinded to a fine powder in a pre-chilled mortar. The powder was transferred to a 15 ml centrifuge tube and added 5 ml buffer AP1 (preheated to 65° C.) and 10 μl RNase A stock solution (100 mg/ml) followed by vigorous vortexing. After incubation for 10 minutes at 65° C. with regular inverting of the tube, 1.8 ml buffer AP2 was added to the lysate by gentle mixing followed by incubation on ice for 10 min. The lysate was then centrifugated at 3000×g for 5 minutes at room temperature and the supernatant was decanted into a QIAshredder maxi spin column placed in a 50 ml collection tube. This was followed by centrifugation at 3000×g for 5 minutes at room temperature. The flow-through was transferred into a new 50 ml tube and added 1.5 volumes of buffer AP3/E followed by vortexing. 15 ml of the sample was transferred into a DNeasy Maxi spin column placed in a 50 ml collection tube and centrifuged at 3000×g for 5 minutes at room temperature. The flow-through was discarded and 12 ml buffer AW was added to the DNeasy Maxi spin column placed in a 50 ml collection tube and centrifuged at 3000×g for 10 minutes at room temperature. After discarding the flow-through, centrifugation was repeated to dispose of the remaining alcohol. The DNeasy Maxi spin column was transferred to a new 50 ml tube and 0.5 ml buffer AE (preheated to 70° C.) was added. After incubation for 5 minutes at room temperature, the sample was eluded by centrifugation at 3000×g for 5 minutes at room temperature. Elution was repeated with an additional 0.5 ml buffer AE and the eluates were combined. The concentration of the harvested DNA was measured by a UV spectrophotometer at 260 nm.

Construction of an *Aspergillus oryzae* Expression Vector Containing *Neurospora crassa* Strain FGSC987 Genomic Sequence Encoding a Family GH16 Polypeptide Having Endo-β-1,3-Galactanase Activity Based on the genome sequence of Swissprot entry Q7RZX8 annotated as a GH16 predicted protein derived from the *Neurospora crassa* genome sequence (Broad Institute, Cambridge, MA, USA), two synthetic oligonucleotide primers shown below were designed to PCR amplify the *Neurospora crassa* Strain FGSC987 P24HN2 gene from the genomic DNA prepared above. An IN-FUSION™ Cloning Kit (BD Biosciences, Palo Alto, CA, USA) was used to clone the fragment directly into the expression vector pDau109 (WO 2005/042735).

F-P24HN2
(SEQ ID NO: 5)
5'-ACACAACTGGGGATCCACCATGAGGAGGTCCTTCCAACAACCC-3'

R-P24HN2
(SEQ ID NO: 6)
5'-CCCTCTAGATCTCGAGTGGACATCTTGAAGGGACAACTCCT-3'

Bold letters represent gene sequence. The underlined sequence is homologous to the insertion sites of pDau109.

An MJ Research PTC-200 DNA engine was used to perform the PCR reaction. A Phusion® High-Fidelity PCR Kit (Finnzymes Oy, Espoo, Finland) was used for the PCR amplification. The PCR reaction was composed of 10 μl of 5×HF buffer (Finnzymes Oy, Espoo, Finland), 1 μl of dNTPs (10 mM), 0.5 μl of Phusion® DNA polymerase (2 units/μl) (Finnzymes Oy, Espoo, Finland), 2 μl of primer F-P24HN2 (2.5 μM), 2 μl of primer R-P24HN2 (2.5 μM), 2 μl of *Neurospora crassa* genomic DNA (100 ng/μl), and 32.5 μl of deionized water in a total volume of 50 μl. The PCR conditions were 1 cycle at 95° C. for 2 minutes. 35 cycles each at 98° C. for 10 seconds, 60° C. for 30 seconds, and 72° C. for 2 minutes; and 1 cycle at 72° C. for 10 minutes. The sample was then held at 12° C. until removed from the PCR machine.

The reaction products were isolated by 1.0% agarose gel electrophoresis using 40 mM Tris base, 20 mM sodium acetate, 1 mM disodium EDTA (TAE) buffer where a 1077 bp product band was excised from the gel and purified using an illustra GFX® PCR DNA and Gel Band Purification Kit (GE Healthcare Life Sciences, Brondby, Denmark) according to the manufacturer's instructions. The fragment was then cloned into Bam HI and Xho I digested pDau109 using an IN-FUSION™ Cloning Kit resulting in plasmid pP24HN2. Cloning of the P24HN2 gene into Bam HI-Xho I digested pDau109 resulted in the transcription of the *Neurospora crassa* P24HN2 gene under the control of a NA2-tpi double promoter. NA2-tpi is a modified promoter from the gene encoding the *Aspergillus niger* neutral alpha-amylase in which the untranslated leader has been replaced by an untranslated leader from the gene encoding the *Aspergillus nidulans* triose phosphate isomerase.

The cloning protocol was performed according to the IN-FUSION™ Cloning Kit instructions generating a P24HN2 GH16 construct. The treated plasmid and insert were transformed into One Shot® TOP10F' Chemically Competent *E. coli* cells (Invitrogen, Carlsbad, CA, USA) according to the manufacturer's protocol and plated onto LB plates supplemented with 0.1 mg of ampicillin per ml. After incubating at 37° C. overnight, colonies were seen growing under selection on the LB ampicillin plates. Two colonies transformed with the P24HN2 GH16 construct were cultivated in LB medium supplemented with 0.1 mg of ampicillin per ml and plasmid was isolated with a QIAprep Spin Miniprep Kit (QIAGEN Inc., Valencia, CA, USA) according to the manufacturer's protocol.

Isolated plasmids were sequenced with vector primers and P24HN2 gene specific primers in order to determine a representative plasmid expression clone that was free of PCR errors.

Characterization of the *Neurospora crassa* FGSC987 Genomic Sequence Encoding a GH16 Polypeptide Having Endo-β-1,3-Galactanase Activity DNA sequencing of the *Neurospora crassa* FGSC987 P24HN2 GH16 genomic clone was performed with an Applied Biosystems Model 3700 Automated DNA Sequencer using version 3.1 BIG-DYE™ terminator chemistry (Applied Biosystems, Inc., Foster City, CA, USA) and primer walking strategy. Nucleotide sequence data were scrutinized for quality and all sequences were compared to each other with assistance of PHRED/PHRAP software (University of Washington, Seattle, WA, USA).

The nucleotide sequence and deduced amino acid sequence of the *Neurospora crassa* P24HN2 gene is shown in SEQ ID NO: 7 and SEQ ID NO: 8, respectively. The coding sequence is 1025 bp including the stop codon and is interrupted by two introns. The encoded predicted protein is 265 amino acids. Using the SignalP program (Nielsen et al., 1997, *Protein Engineering* 10: 1-6), a signal peptide of 27 residues was predicted. The predicted mature protein contains 238 amino acids with a predicted molecular mass of 26 kDa and an isoelectric pH of 9.3.

A comparative pairwise global alignment of amino acid sequences was determined using the Needleman and Wunsch algorithm (Needleman and Wunsch, 1970, *J. Mol. Biol.* 48: 443-453) with gap open penalty of 10, gap extension penalty of 0.5, and the EBLOSUM62 matrix. The alignment showed that the deduced amino acid sequence of the *Neurospora crassa* gene encoding the P24HN2 GH16 polypeptide having endo-beta-1,3-galactanase activity shares 97% identity (excluding gaps) to the deduced amino acid sequence of a putative uncharacterized GH16 family protein from *Neurospora tetrasperma* (accession number SWISSPROT: F8MMR0).

Expression of the *Neurospora crassa* GH16 Endo-β-1,3-Galactanase GALACTANASE3

The expression plasmid pP24HN2 was transformed into *Aspergillus oryzae* MT3568. *Aspergillus oryzae* MT3568 is an AMDS (acetamidase) disrupted derivative of JaL355 (WO 02/40694) in which pyrG auxotrophy was restored in the process of knocking out the *Aspergillus oryzae* acetamidase (AMDS) gene. MT3568 protoplasts are prepared according to the method of European Patent No. 0238023, pages 14-15, which are incorporated herein by reference.

Transformants were purified on COVE sucrose selection plates through single conidia prior to sporulating them on PDA plates. Production of the *Neurospora crassa* GH16 polypeptide by the transformants was analyzed from culture supernatants of 1 ml 96 deep well stationary cultivations at 30° C. in YP+2% glucose medium. Expression was verified on an E-Page 8% SDS-PAGE 48 well gel (Invitrogen, Carlsbad, CA, USA) by Coomassie staining. One transformant was selected for further work and designated *Aspergillus oryzae* 90.1.

For larger scale production, *Aspergillus oryzae* 90.1 spores were spread onto a PDA plate and incubated for five days at 37° C. The confluent spore plate was washed twice with 5 ml of 0.01% TWEEN® 20 to maximize the number of spores collected. The spore suspension was then used to inoculate fifteen 500 ml flasks containing 150 ml of Dap-4C medium. The culture was incubated at 30° C. with constant shaking at 100 rpm. At day four post-inoculation, the culture broth was collected by filtration through a bottle top MF75 Supor MachV 0.2 μm PES filter (Thermo Fisher Scientific, Roskilde, Denmark). Fresh culture broth from this transformant produced a band of GH16 protein of approximately 26 kDa. The identity of the prominent band as the *Neurospora crassa* GH16 polypeptide was verified by peptide sequencing.

Alternative Method for Producing the *Neurospora crassa* GH16 Endo-β-1,3-Galactanase GALACTANASE3

Based on the nucleotide sequence identified as SEQ ID NO: 7, a synthetic gene can be obtained from a number of vendors such as Gene Art (GENEART AG BioPark, Josef-EngertStr. 11, 93053, Regensburg, Germany) or DNA 2.0 (DNA2.0, 1430 O'Brien Drive, Suite E, Menlo Park, CA 94025, USA). The synthetic gene can be designed to incorporate additional DNA sequences such as restriction sites or homologous recombination regions to facilitate cloning into an expression vector.

Using the two synthetic oligonucleotide primers F-P24HN2 and F-P24HN2 described above, a simple PCR reaction can be used to amplify the full-length open reading frame from the gene of SEQ ID NO: 7. The gene can then be cloned into an expression vector for example as described above and expressed in a host cell, for example in *Aspergillus oryzae* as described above.

Purification of the *Neurospora crassa* Endo-β-1,3-Galactanase (GALACTANASE3)

The harvested cell culture broth of the *Neurospora crassa* was supplemented with 1.5 M ammonium sulphate to a final concentration of 1.5 M and pH was adjusted to 8. The sample was then loaded on a hydrophobic column (packed bed of butyl Toyo pearl; gradient: 0-100% B in 10 column volumes; buffer A: 50 mM Mes and 1.5 M ammonium sulphate; buffer B: 50 mM Mes). SDS-PAGE (reducing conditions) confirmed that the galactanase was not eluted through the column in the flow-through or wash fraction. Based on the SDS-PAGE, fractions containing proteins of the expected Mw of 28.9 kDa (fractions 34-48) were pooled, concentrated and buffer-exchanged into 20 mM sodium acetate buffer pH 6.5 by centrifugation in viva spin column 3 kDa MWCO membrane (3000×g spin centrifugation).

Example 4

Cloning, Expression and Purification of the *Irpex lacteus* GH43 Exo-β-1,3-Galactanase (GALACTANASE4)

Construction of an *Aspergillus oryzae* Expression Vector Containing *Irpex lacteus* Strain cDNA Sequence Encoding a Family GH43 Polypeptide Having Exo-β-1,3-Galactanase Activity Based on the nucleotide sequence EMBL:AB461394, a synthetic gene P24QQC (SEQ ID NO: 9) was obtained from GeneArt (Invitrogen, Carlsbad, CA, USA) encoding the cDNA of the *Irpex lacteus* exo-beta-1,3-galactanase with additional BamHI and XhoI restriction sites to facilitate cloning into an expression vector.

The GeneArt construct containing P24QQC was treated with BamHI and XhoI restriction enzymes and the reaction products were isolated by 1.0% agarose gel electrophoresis using 40 mM Tris base, 20 mM sodium acetate, 1 mM disodium EDTA (TAE) buffer where a 1360 bp product band was excised from the gel and purified using an illustra GFX® PCR DNA and Gel Band Purification Kit (GE Healthcare Life Sciences, Brondby, Denmark) according to the manufacturer's instructions. The fragment was then cloned into Bam HI and Xho I digested pDau109 using an IN-FUSION™ Cloning Kit resulting in plasmid pP24QQC. Cloning of the P24QQC gene into Bam HI-Xho I digested pDau109 resulted in the transcription of the *Irpex lacteus* P24QQC gene under the control of a NA2-tpi double promoter. NA2-tpi is a modified promoter from the gene encoding the *Aspergillus niger* neutral alpha-amylase in which the untranslated leader has been replaced by an untranslated leader from the gene encoding the *Aspergillus nidulans* triose phosphate isomerase.

The cloning protocol was performed according to the IN-FUSION™ Cloning Kit instructions generating a P24QQC GH43 construct. The treated plasmid and insert were transformed into One Shot® TOP10F' Chemically Competent *E. coli* cells (Invitrogen, Carlsbad, CA, USA) according to the manufacturer's protocol and plated onto LB plates supplemented with 0.1 mg of ampicillin per ml. After incubating at 37° C. overnight, colonies were seen growing under selection on the LB ampicillin plates. Two colonies transformed with the P24QQC GH43 construct were cultivated in LB medium supplemented with 0.1 mg of ampicillin per ml and plasmid was isolated with a QIAprep Spin Miniprep Kit (QIAGEN Inc., Valencia, CA, USA) according to the manufacturer's protocol.

Isolated plasmids were sequenced with vector primers and P24QQC gene specific primers in order to determine a representative plasmid expression clone that was free of PCR errors.

Characterization of the *Irpex lacteus* cDNA Sequence Encoding a GH43 Polypeptide Having Exo-β-1,3-Galactanase Activity DNA sequencing of the *Irpex lacteus* P24QQC GH43 cDNA clone was performed with an Applied Biosystems Model 3700 Automated DNA Sequencer using version 3.1 BIG-DYE™ terminator chemistry (Applied Biosystems, Inc., Foster City, CA, USA) and primer walking strategy.

Nucleotide sequence data were scrutinized for quality and all sequences were compared to each other with assistance of PHRED/PHRAP software (University of Washington, Seattle, WA, USA).

The nucleotide sequence and deduced amino acid sequence of the *Irpex lacteus* P24QQC gene is shown in SEQ ID NO: 9 and SEQ ID NO: 10, respectively. The coding sequence is 1347 bp including the stop codon. The encoded predicted protein is 448 amino acids. Using the SignalP program (Nielsen et al., 1997, *Protein Engineering* 10: 1-6), a signal peptide of 20 residues was predicted. The predicted mature protein contains 428 amino acids with a predicted molecular mass of 46 kDa and an isoelectric pH of 6.1. Amino acids 337-448 is a putative CBM35.

Expression of the *Irpex lacteus* GH43 Exo-β-1,3-Galactanase (GALACTANASE4)

The expression plasmid pP24QQC was transformed into *Aspergillus oryzae* MT3568. *Aspergillus oryzae* MT3568 is an AMDS (acetamidase) disrupted derivative of JaL355 (WO 02/40694) in which pyrG auxotrophy was restored in the process of knocking out the *Aspergillus oryzae* acetamidase (AMDS) gene. MT3568 protoplasts are prepared according to the method of European Patent No. 0238023, pages 14-15, which are incorporated herein by reference.

Transformants were purified on COVE sucrose selection plates through single conidia prior to sporulating them on PDA plates. Production of the *Irpex lacteus* GH43 polypeptide by the transformants was analyzed from culture supernatants of 1 ml 96 deep well stationary cultivations at 30° C. in YP+2% glucose medium. Expression was verified on an E-Page 8% SDS-PAGE 48 well gel (Invitrogen, Carlsbad, CA, USA) by Coomassie staining. One transformant was selected for further work and designated *Aspergillus oryzae* 433.1.

For larger scale production, *Aspergillus oryzae* 433.1 spores were spread onto a PDA plate and incubated for five days at 37° C. The confluent spore plate was washed twice with 5 ml of 0.01% TWEEN® 20 to maximize the number of spores collected. The spore suspension was then used to inoculate fifteen 500 ml flasks containing 150 ml of Dap-4C medium (WO 2012/103350). The culture was incubated at 30° C. with constant shaking at 100 rpm. At day four post-inoculation, the culture broth was collected by filtration through a bottle top MF75 Supor MachV 0.2 μm PES filter (Thermo Fisher Scientific, Roskilde, Denmark). Fresh culture broth from this transformant produced a band of GH43 protein of approximately 46 kDa. The identity of the band as the *Irpex lacteus* GH43 polypeptide was verified by peptide sequencing.

Purification of the *Irpex lacteus* GH43 Exo-β-1,3-Galactanase

Filtrated broth was adjusted to pH 7.5 and filtrated on 0.22 μm PES filter (Nalge Nunc International, Nalgene labware cat #595-4520). Following, the filtrate was added 1.8 M ammonium sulphate. The filtrate was loaded onto a Phenyl Sepharose™ 6 Fast Flow column (high sub) (GE Healthcare, Piscataway, NJ, USA) equilibrated with 1.8 M ammonium sulphate, 25 mM HEPES pH 7.5. After wash with 1.0 M ammonium sulphate, the bound proteins were batch eluted with 25 mM HEPES pH 7.5. Fractions were collected and analyzed by SDS-PAGE. The fractions were pooled and applied to a Sephadex™ G-25 (medium) (GE Healthcare, Piscataway, NJ, USA) column equilibrated in 25 mM HEPES pH 7.5. The fractions were applied to a SOURCE™ 15Q (GE Healthcare, Piscataway, NJ, USA) column equilibrated in 25 mM HEPES pH 7.5 and bound proteins were eluted with a linear gradient from 0-1000 mM sodium chloride over 20 CV. The protein did not bind to the column, and the eluate was concentrated using ultrafiltration on a 30,000 MWCO PES Vivaspin 20 filter (Sartorius Stedim Biotech GmbH, Goettingen, Germany), and the concentrate was analyzed by SDS-PAGE.

Example 5

Cloning, Expression and Purification of the *Ignisphaera aggregans* GH53 Endo-β-1,4-Galactanase (BETA-1,4-GALACTANASE)

Construction of an *Aspergillus oryzae* Expression Vector Containing *Ignisphaera aggregans* DNA Sequence Encoding a Family GH53 Polypeptide Having Endo-β-1,4-Galactanase Activity Based on the nucleotide sequence UNIPROT:EOSSW8, a codon-optimized gene for *A. oryzae* expression encoding a C-terminal truncated endo-β-1,4-galactanase (SEQ ID NO: 11) was generated based on a similar algorithm developed by Gustafsson et al, 2004*. The synthetic gene (SEQ ID NO: 11) covering nucleotides 1 to 1221 of the nucleotide sequence UNIPROT:EOSSW8 was obtained from GeneArt (Invitrogen, Carlsbad, CA, USA) encoding the DNA of the *Ignisphaera aggregans* C-terminal truncated endo-β-1,4-galactanase with a 5' prime BamHI restriction site, a 3' prime stop codon HindIII restriction site, and a Kozac consensus sequence (CACC) situated between the start codon and the BamHI restriction site.

The GeneArt construct containing the synthetic endo-β-1,4-galactanase gene was treated with BamHI and HindIII restriction enzymes and the reaction products were isolated by 1.0% agarose gel electrophoresis using 40 mM Tris base, 20 mM sodium acetate, 1 mM disodium EDTA (TAE) buffer where a 1239 bp product band was excised from the gel and purified using an illustra GFX® PCR DNA and Gel Band Purification Kit (GE Healthcare Life Sciences, Brondby, Denmark) according to the manufacturer's instructions. The 1239 bp fragment was then cloned into pDau109 (WO 2005/042735) digested with BamHI and HindIII using a T4 DNA ligase (New England Biolabs, Ipswich, MA, USA). The BamHI-HindIII digested pDau109 and the BamHI/HindIII fragment containing the endo-β-1,4-galactanase coding sequence were mixed in a molar ratio of 1:3 (i.e., mass ratio approximately 2.5:1 or 20 ng:50 ng) and ligated with 50 U of T4 DNA ligase in 1×T4 DNA ligase buffer (New England Biolabs, Ipswich, MA, USA) with 1 mM ATP at 16° C. over-night in accordance with the manufacturer's instructions.

Cloning of the synthetic endo-β-1,4-galactanase gene into BamHI-HindIII digested pDau109 resulted in the transcription of the *Ignisphaera aggregans* endo-β-1,4-galactanase gene under the control of a NA2-tpi double promoter. NA2-tpi is a modified promoter from the gene encoding the *Aspergillus niger* neutral alpha-amylase in which the untranslated leader has been replaced by an untranslated leader from the gene encoding the *Aspergillus nidulans* triose phosphate isomerase.

The treated plasmid and insert were transformed into One Shot® TOP10F' Chemically Competent *E. coli* cells (Invitrogen, Carlsbad, CA, USA) according to the manufacturer's protocol and plated onto LB plates supplemented with 0.1 mg of ampicillin per ml. After incubating at 37° C. over-night, colonies were seen growing under selection on the LB ampicillin plates.

Insertion of the *Ignisphaera aggregans* endo-β-1,4-galactanase gene into pDau109 was verified by PCR on colonies as described below using the following primers.

```
Primer F-pDau109 (SEQ ID NO: 13):
5'-CCCTTGTCGATGCGATGTATC-3'

Primer R-pDau109 (SEQ ID NO: 14):
5'-ATCCTCAATTCCGTCGGTCGA-3'
```

A 1.1× REDDYMIX® Master Mix (Thermo Fisher Scientific, Roskilde, Denmark) was used for the PCR amplification. The PCR reaction was composed of 10 µl of 1.1× REDDYMIX® Master Mix, 0.5 µl of primer F-pDau109 (10 µM), and 0.5 µl of primer R-pDau109 (10 µM). A toothpick was used to transfer a small amount of cells to the PCR solution. The PCR was performed using a PTC-200 DNA Engine programmed for 1 cycle at 94° C. for 2 minutes 30 seconds; 30 cycles each at 94° C. for 15 seconds, 60° C. for 30 seconds, and 68° C. for 1 minute 30 seconds; and 1 cycle at 68° C. for 7 minute. The sample was then held at 10° C. until removed from the PCR machine.

The PCR reaction products were analyzed by 1.0% agarose gel electrophoresis using TAE buffer where a 1541 bp PCR product band was observed confirming insertion of the *Ignisphaera aggregans* endo-β-1,4-galactanase coding sequence into pDau109.

An *E. coli* transformant containing the *Ignisphaera aggregans* endo-β-1,4-galactanase GH53 construct were cultivated in LB medium supplemented with 0.1 mg of ampicillin per ml and plasmid was isolated with a QIAprep Spin Miniprep Kit (QIAGEN Inc., Valencia, CA, USA) according to the manufacturer's protocol. The plasmid was designated pBETA-1,4-GALACTANASE.

Characterization of the DNA Sequence Encoding *Ignisphaera aggregans* Endo-β-1,4-Galactanase GH53 Polypeptide The nucleotide sequence and deduced amino acid sequence of the *Ignisphaera aggregans* endo-β-1,4-galactanase gene is shown in SEQ ID NO: 11 and SEQ ID NO: 12, respectively. The coding sequence is 1224 bp including the stop codon. The encoded predicted protein is 407 amino acids. Using the SignalP program (Nielsen et al., 1997, *Protein Engineering* 10: 1-6), a signal peptide of 26 residues was predicted. The predicted mature protein contains 381 amino acids with a predicted molecular mass of 43 kDa and an isoelectric pH of 4.8.

Expression of the *Ignisphaera aggregans* GH53 Endo-β-1, 4-Galactanase (BETA-1,4-GALACTANASE)

The expression plasmid was transformed into *Aspergillus oryzae* MT3568. *Aspergillus oryzae* MT3568 is an AMDS (acetamidase) disrupted derivative of JaL355 (WO 02/40694) in which pyrG auxotrophy was restored in the process of knocking out the *Aspergillus oryzae* acetamidase (AMDS) gene. MT3568 protoplasts are prepared according to the method of European Patent No. 0238023, pages 14-15, which are incorporated herein by reference.

Transformants were purified on COVE sucrose selection plates through single conidia prior to sporulating them on PDA plates. Production of the *Ignisphaera aggregans* GH53 polypeptide by the transformants was analyzed from culture supernatants of 1 ml 96 deep well stationary cultivations at 30° C. in YP+2% glucose medium. Expression was verified on an E-Page 8% SDS-PAGE 48 well gel (Invitrogen, Carlsbad, CA, USA) by Coomassie staining. One transformant was selected for further work and designated KHJN0032-3.

For larger scale production, KHJN0032-3 spores were spread onto a PDA plate and incubated for five days at 37° C. The confluent spore plate was washed twice with 5 ml of 0.01% TWEEN® 20 to maximize the number of spores collected. The spore suspension was then used to inoculate fifteen 500 ml flasks containing 150 ml of Dap-4C medium (WO 2012/103350). The culture was incubated at 30° C. with constant shaking at 100 rpm. At day five post-inoculation, the culture broth was collected by filtration through a bottle top MF75 Supor MachV 0.2 µm PES filter (Thermo Fisher Scientific, Roskilde, Denmark). Fresh culture broth from this transformant produced a band of GH43 protein of approximately 43 kDa.

Purification of the *Ignisphaera aggregans* GH53 Endo-β-1, 4-Galactanase (BETA-1,4-GALACTANASE)

Filtrated broth was adjusted to pH 7.0 and filtrated on 0.22 µm PES filter (Nalge Nunc International, Nalgene labware cat #595-4520). Following, the filtrate was added 1.0 M ammonium sulphate. The filtrate was loaded onto a Phenyl Sepharose™ 6 Fast Flow column (high sub) (GE Healthcare, Piscataway, NJ, USA) equilibrated with 1.0 M ammonium sulphate, 25 mM HEPES pH 7.0. The bound proteins were batch eluted with 25 mM HEPES pH 7.0 followed by 50% EtOH. Fractions were collected and analyzed by SDS-PAGE. The fractions were pooled and applied to a Sephadex™ G-25 (medium) (GE Healthcare, Piscataway, NJ, USA) column equilibrated in 25 mM HEPES pH 7.0. The fractions were applied to a SOURCE™ 15Q (GE Healthcare, Piscataway, NJ, USA) column equilibrated in 25 mM HEPES pH 7.0 and bound proteins were eluted with a linear gradient from 0-500 mM sodium chloride. Fractions were collected and analyzed by SDS-PAGE.

Example 6

Synthesis of β-1,3-Galactan Substrates

Different carbohydrates were used as substrates for characterising the β-1,3-galactanases:
a) Gum Arabic Commercially available (Merck). Complex polysaccharide composed of D-galactose (44%); L-arabinose (24%); D-glucuronic acid (14.5%); L-rhamnose (13%); 4-O-methyl-D-glucuronic acid (1.5%). β-1,3-linked galactoses form the backbone.
b) Acid Treated Gum Arabic Gum Arabic was treated with 0.1 M TFA for 1 h at 90° C. The reaction was stopped by adjusting the pH to 7 with 4 M NaOH. The sample was then reduced by $NaBH_4$ (2 mg per mg of polysaccharide) for 3 h at room temperature followed by dialysis overnight. The solid was recovered by freeze drying. TLC confirmed the decrease of arabinose in the polysaccharide.
c) Smith Degraded Gum Arabic Gum Arabic was degraded according to the Smith degradation method described in the literature (Tsumuraya et al., Carbohydrate Research, 1984, 134, 215-228). Gum Arabic side chains (arabinose and β-1,6-linked galactose) were first cleaved by periodate (excess destroyed by ethylene glycol) then reduced by sodium borohydride, and hydrolysed with dilute acid under mild conditions. The procedure was repeated 3 times. NMR confirmed the decrease of arabinose and β-1,6-linked galactoses from the side chains. The oxidation of Gum Arabic (up to 5 g) with 50 mM sodium metaperiodate (up to 500 mL) was carried out in the dark at 4° C. for 48-96 h. The reaction was terminated by addition of ethylene glycol (up to 4 mL) and stirring for 2 h at room temperature. After overnight dialysis (3.5 kDa MWCO, distilled water), reduction of the oxidised product was performed with NaBH$_4$ (2 mg per mg of polysaccharide) for 3 h. The reaction was terminated by making pH 7 with 10% AcOH and dialysing overnight. After evaporating to a small volume, the sample was hydrolysed with diluted TFA (0.5 M) under mild conditions for 24 h at room temperature. After evaporating most of the acid and adjusting the pH to 7 by addition of 1 M NaOH, the substrate was precipitated with 3 volumes of ethanol and recovered by centrifugation and freeze drying. The procedure was repeated 3 times to produce triple Smith degraded Gum Arabic.

Example 7

Reducing Sugar Assay (PAH-BAH Assay) for Quantification of β-1,3-Galactanase Activity β-1,3-Galactanase activity was determined in two steps. The first step is an enzymatic step where carbohydrate substrates are hydrolysed by the catalytic action of the galactanase. The second step is a non-enzymatic detection step where the aldehyde group of the mono- and oligosaccharides are reduced to form a yellow coloured compound.
a) Activity Assay—Degradation of Polysaccharides
  50 μL of a 0.08 g/L enzyme solution (MilliQ water for blank sample) was mixed with 50 μL of Activity buffer (20 mM sodium acetate buffer pH 5) and 50 μL of Substrate solution (5-10 g/L dissolved in MilliQ water) in a 96-well PCR-MTP
  The reaction was carried out at 40° C. for 45 minutes in a PCR machine
  The reaction was stopped by increasing the temperature to 95° C. for 10 minutes
b) Activity Assay—Detection of Reducing Sugars (PAH-BAH—Assay)
  25 μL sample from above was diluted with 100 μL 1 M NaOH in a new 96-well PCR-MTP
  75 μL of a fresh stop solution was added into the well (4-hydroxy benzoic acid hydrazide dissolved in 15 g/L in 2% (w/v) NaOH and 5% (w/v) K—Na-tartrate)
  Reaction was incubated 10 minutes at 70° C.
  Endpoint absorbance was measured at 405 nm
Activity Calculation:

A standard curve for reducing sugars was made with different galactose concentrations ranging from 0.05 g/L to 3 g/L following the procedure above. The following standard equation was obtained: amount of sugar released (measured as μg of galactose equivalents): $m_{gal\ eq}=(A_{405}-0.0061)/0.016$. The observed absorbance of the blank was always subtracted from the obtained absorbance allowing comparison of all the results. The quantity of reducing sugars released after reaction (45 minutes at 40° C.) was calculated according to the standard curve. The enzymatic activity (%) was calculated as the percentage of released galactose equivalents compared to the total mass of the polysaccharide substrate (Table 1).

Example

For an assay with 5 g/L Smith degraded Gum Arabic, the total amount of polysaccharide is 250 μg. After the two-step reaction, a sample absorbance of 2.26 with a blank absorbance of 0.16 corresponds to 131 μg of galactose equivalents giving an observed activity of 52%.

TABLE 1

Relative activity (% galactose reducing end equivalents released per mass of substrate) for degrading Gum arabic and related products

| Enzymes | Smith degraded Gum Arabic | Acid treated Gum Arabic | Gum Arabic |
|---|---|---|---|
| GALACTANASE1 | 52.7 | 9.2 | 2.6 |
| GALACTANASE2 | 43.6 | 0.5 | 0.2 |
| GALACTANASE3 | 46.2 | 9.3 | 2.7 |
| GALACTANASE4 | 25.6 | 17.7 | 2.4 |

The decrease of side chains on the substrate increases the galactanase activity.

Example 8

TLC Assay for Detection of β-1,3-Galactanase Activity

The heat inactivated reaction mixture (Example 7a) was analysed by TLC (Silica gel 60 F254) to characterize the enzymes with regards to endo and exo activity. The eluent was butan-1-ol, ethanol and water (5/5/4 v/v). Reference compounds were arabinose ($Rf_{ara}$=0.56); galactose ($Rf_{Gal}$=0.53); β-1,4-galactobiose ($Rf_{Gal2}$=0.50) and β-1,6-galactotetraose ($Rf_{Gal4}$=0.44). The expected reaction product β-1,3-galactobiose was expected to migrate with similar Rf as β-1,4-galactobiose, and β-1,3-galactotetraose was assumed to migrate with similar Rf as β-1,6-galactotetraose. Results are shown in Table 2.

TABLE 2

Relative activity (% galactose reducing end equivalents released per mass of substrate)and product composition for degradation of β-1,3-Galactan (triple Smith degraded Gum Arabic) by 4 galactanases

| | Smith degraded Gum Arabic | | | |
|---|---|---|---|---|
| Enzymes | GALAC-TANASE1 | GALAC-TANASE2 | GALAC-TANASE3 | GALAC-TANASE4 |
| % Activity | 52.7 | 43.6 | 46.2 | 25.6 |
| Arabinose | − | − | − | − |
| Galactose | ++ | ++ | ++ | +++ |
| Galactobiose | +++ | +++ | +++ | + |
| Galactotetraose | ++ | ++ | ++ | − |

The release of arabinose, galactose, galactobiose and galactotetraose was detected by TLC. (−) means no spot on the plate, and (+), (++), (+++) indicate a spot with different intensity (the more +, the more intense the spot). The product composition justifies primarily endo activity of GALACTANASE1,GALACTANASE2 and GALACTANASE3 and exo activity of GALACTANASE4.

Example 9 pH Optima and pH Stability of Galactanases pH stability of GALACTANASE1 and GALACTANASE4 (0.08 g/L) was evaluated by determining the enzymatic activity by the reducing sugar assay (Example 7) after incubation with a substrate solution (2.5 g/L Smith degraded Gum Arabic or 15 g/L acid treated Gum Arabic) for 45 minutes at 40° C. at selected pH values in the interval 1.5-10. The activity of the galactanases was tested right after adjusting the pH (t0), or after incubating the enzyme at the given pH for 24 h in the fridge before addition of the substrate (24 h) (Tables 3 and 4). The pH was measured before and after reaction to confirm that the pH was constant during the incubation.

TABLE 3

Activity buffer composition, pH was adjusted according to the wanted pH

| pH | Employed buffer |
|---|---|
| 1.5; 2; 2.5 | 60 mM KCl/HCl |
| 3; 3.6; 3.9; 4.3; 4.7; 5; 5.2; 5.7 | 20 mM Sodium acetate |
| 6 | 50 mM Mes |
| 7 and 8 | 50 mM HEPES |
| 9 and 10 | 50 mM Tris HCl |

TABLE 4

Observed activity (%) at different pH values

| | Activity GALACTANASE1 Substrate | | | Activity GALACTANASE4 | | |
|---|---|---|---|---|---|---|
| | Smith degraded Gum Arabic | | Acid treated Gum Arabic | Smith degrade Gum Arabic | | Acid treated Gum Arabic |
| pH | t0 | 24 h | t0 | t0 | 24 h | t0 |
| 1.5 | 0.9 | 0.0 | 0.0 | 0.5 | 0.0 | 0.0 |
| 2 | 27.4 | 1.5 | 2.3 | 1.6 | 0.6 | 1.8 |
| 2.5 | 40.2 | 31.4 | 2.6 | 6.1 | 2.0 | 8.8 |
| 3 | 42.5 | 32.9 | 6.8 | 13.6 | 8.3 | 17.1 |
| 3.6 | 42.6 | 27.2 | 10.0 | 19.1 | 8.5 | 18.3 |
| 3.9 | 44.5 | 37.6 | 10.2 | 19.2 | 9.4 | 18.0 |
| 4.3 | 40.9 | 45.1 | 9.7 | 19.5 | 9.4 | 17.2 |
| 4.6 | 43.6 | 43.0 | 9.5 | 18.8 | 8.0 | 16.4 |
| 5.1 | 45.7 | 38.4 | 8.3 | 19.3 | 8.3 | 13.9 |
| 5.7 | 40.8 | 36.9 | 7.5 | 16.6 | 8.6 | 9.1 |
| 6 | 39.4 | 40.7 | 6.8 | 15.2 | 8.2 | 8.6 |
| 7 | 36.3 | 39.8 | 3.3 | 9.5 | 4.5 | 2.1 |
| 8 | 19.1 | 20.9 | 0.2 | 0.5 | 0.1 | 0.0 |
| 9 | 2.6 | 2.3 | 0.0 | 0.8 | 0.2 | 0.0 |
| 10 | 0.0 | 0.5 | 0.0 | 0.4 | 0.1 | 0.0 |

Example 10

Thermostability of Galactanases Evaluated by DSC

Thermostabilities of GALACTANASE1, GALACTANASE2, GALACTANASE3 and GALACTANASE4 were evaluated by Differential Scanning calorimetry (DSC) in the appropriate buffer solution (20 mM Sodium acetate pH 6.5). The temperature corresponding to the apex of the peak in the thermogram was noted as the thermal transition midpoint ($T_m$ (° C.)) for the enzymes.

TABLE 5

Midpoint temperatures

| Enzyme | Temperature ° C. |
|---|---|
| GALACTANASE1 | 66.2 |
| GALACTANASE2 | 58.0 |
| GALACTANASE3 | 62.3 |
| GALACTANASE4 | 43.1 |

Example 11

Thermostability of Galactanases Evaluated by Reducing Sugar Assay at Different Temperatures Thermostabilities of GALACTANASE1 and GALACTANASE4 (0.04 g/L) were evaluated by determining the enzymatic activity by the reducing sugar assay (Example 7) after incubation with 2.5 g/L substrate solution (Smith degraded Gum Arabic) for 45 minutes at pH 5 at selected temperatures in the interval 20° C.-90° C. The enzyme was added to the assay after the sample (buffer and substrate solution) was heated to the selected temperature. Temperature optima of 60° C. (GALACTANASE1) and 30° C. (GALACTANASE4) were observed (Table 6).

TABLE 6

Observed activity (%) at different temperatures

| Temperature (° C.) | Activity GALACTANASE1 | Activity GALACTANASE4 |
|---|---|---|
| 20 | 44.1 | 19.9 |
| 30 | 42.9 | 20.2 |
| 40 | 41.5 | 20.2 |
| 50 | 38.0 | 18.5 |
| 60 | 50.1 | 16.6 |
| 70 | 44.8 | 13.4 |
| 80 | 47.9 | 4.5 |
| 90 | 17.3 | 0.3 |

Example 12

Pretreatment of Coffee Material 800 mL boiling water was added to 155 g roasted and grinded *Arabica* coffee beans with a particle size of 0.5 mm. After incubation in a water bath at 95° C. for 30 min with manual mixing every 5 min, the slurry was cooled down at room temperature. After an initial vacuum filtration through a Whatman GF/D filter, Ø 150 mm., the insoluble spent coffee on the filter was washed by adding 500-1000 mL MilliQ water. The spent coffee was removed from the filter and spread out on a large sheet and left to dry overnight. This fraction was called spent coffee grounds and used in Example 14.

The spent coffee grounds were further defatted by water saturated butanol. The butanol fraction was separated by filtration and the defatted spent coffee grounds were dried under vacuum before use. This defatted spent coffee grounds were used in Example 13.

Example 13

Enzyme Catalyzed Hydrolysis of Defatted Spent Coffee Grounds a) Enzymatic Extraction Defatted spent coffee grounds produced according to Example 12 (10 weight %) was incubated with water and a suitably diluted enzyme (to give a final reaction concentration of 0.05 g/L for the galactanases and 0.2 volume % for Mannaway® 25L at 40° C. (for GALACTANASE1-4) or at 80° C. (for the BETA-1,4-GALACTANASE). Samples were withdrawn after 2 and 24 hours and the enzymatic hydrolysis was stopped immediately by heating the samples at 100° C. for 10 min. After centrifugation (10,000×g, 10 min) and filtration through a 0.22 µm filter, the supernatants were further analyzed for dry matter, carbohydrate composition and absorbance. The procedures were performed in duplicate for all enzymes and a blank (no enzyme).

b) Dry Matter Determination

Dry matter (DM) content was quantified after overnight drying at 110° C. of supernatants from enzyme treated spent coffee grounds. The weight of the dry matter was divided by the added volume of supernatant and a DM value based on g/L was calculated. The characteristics of the extract based on DM are summarized in Table 7. The synergy effect was calculated by dividing the observed value of the combined treatment with the theoretical value. The theoretical value is calculated by adding the DM of the individual enzyme treatments (β-1,3-galactanase and mannanase treatments) and subtracting the DM of the treatment with no enzyme.

TABLE 7

Dry matter of defatted spent grounds extract after different enzymatic treatments.

| Enzyme treatment | Dry matter (g/L) | | Synergy effect (%) | |
|---|---|---|---|---|
| | 2 h | 24 h | 2 h | 24 h |
| No enzyme | 1.5 | 2.4 | — | — |
| Mannaway | 3.0 | 7.0 | — | — |
| GALACTANASE1 | 9.2 | 13.8 | — | — |
| GALACTANASE2 | 3.6 | 7.2 | — | — |
| GALACTANASE3 | 5.4 | 8.3 | — | — |
| GALACTANASE4 | 5.2 | 7.7 | — | — |
| Mannaway + GALACTANASE1 | 14.5 | 25.5 | 136 | 139 |
| Mannaway + GALACTANASE2 | 7.9 | 15.9 | 154 | 135 |
| Mannaway + GALACTANASE3 | 10.6 | 18.3 | 153 | 142 |
| Mannaway + GALACTANASE4 | 9.6 | 16.5 | 144 | 134 |

The yield of soluble solids was substantially greater when Mannaway was incubated together with any of the β-1,3-galactanases, as compared to when the enzymes were incubated alone. With this substrate and under the investigated conditions, the synergy effect varied between 134-154%.

Under the same experimental setup but at a higher temperature (80° C.), BETA-1,4-GALACTANASE was incubated with the defatted spent grounds (Table 8). However, addition of this type of galactanase did not have any significant effect at the conditions and enzyme dosages applied in the present study.

TABLE 8

Dry matter of defatted spent grounds extract after treatment by a *Ignisphaera aggregans* endo-β-1,4-galactanase.

| Enzyme treatment | Dry matter (g/L) | |
|---|---|---|
| | 2 h | 24 h |
| No enzyme | 1.5 | 4.1 |
| BETA-1,4-GALACTANASE | 2.4 | 3.8 | c) Carbohydrate Analysis

The sugar composition was analysed by measuring free monosaccharides in the supernatants by high-performance anion exchange chromatography with pulsed amperometric detection (HPAEC-PAD). The total sugars were analysed by HPAEC-PAD after acid hydrolysis in 2 M trifluoro acetic acid for 2 h at 95° C. The acid hydrolysed samples were neutralised by an initial dilution in 0.2 M NaOH. Monosaccharides were quantified after suitable dilutions against a 5-point standard curve of arabinose (Ara), galactose (Gal), glucose (Glc) and mannose (Man) between 0.002-0.02 g/L. The results can be seen in Tables 9 and 10.

TABLE 9

Free monosaccharides in the extract from defatted spent coffee grounds after enzymatic treatment.

| | Free monosaccharides/DM (%) | | | |
|---|---|---|---|---|
| | 2 h | | 24 h | |
| Enzyme treatment | Gal | Man | Gal | Man |
| No enzyme | 0 | 0 | 0 | 0 |
| Mannaway | 0 | 1 | 0 | 1 |
| GALACTANASE1 | 4 | 0 | 6 | 0 |
| GALACTANASE2 | 1 | 0 | 2 | 0 |
| GALACTANASE3 | 1 | 0 | 1 | 0 |
| GALACTANASE4 | 18 | 0 | 16 | 0 |
| Mannaway + GALACTANASE1 | 2 | 0 | 3 | 1 |
| Mannaway + GALACTANASE2 | 1 | 1 | 1 | 1 |
| Mannaway + GALACTANASE3 | 1 | 0 | 1 | 1 |
| Mannaway + GALACTANASE4 | 9 | 1 | 8 | 1 |

The extracts from treatment with the endo-acting enzymes (Mannaway and GALACTANASE1, GALACTANASE2, GALACTANASE3) contained relatively low amounts of monosaccharides, in contrast to treatment with the exo-acting galactanase (GALACTANASE4).

TABLE 10

Total sugar composition in the extract from defatted spent coffee grounds after enzymatic treatment. Monosaccharides in supernatant after acid hydrolysis.

| | Total monosaccharides/DM (%) | | | | | | | |
|---|---|---|---|---|---|---|---|---|
| | 2 h | | | | 24 h | | | |
| Enzyme treatment | Ara | Gal | Glc | Man | Ara | Gal | Glc | Man |
| No enzyme | 0 | 13 | 0 | 26 | 8 | 8 | 8 | 25 |
| Mannaway | 0 | 7 | 7 | 46 | 3 | 9 | 3 | 46 |
| GALACTANASE1 | 13 | 72 | 0 | 4 | 10 | 55 | 1 | 6 |
| GALACTANASE2 | n.d. | n.d. | n.d. | n.d. | 8 | 44 | 3 | 11 |
| GALACTANASE3 | 11 | 55 | 0 | 7 | 10 | 48 | 2 | 7 |

TABLE 10-continued

Total sugar composition in the extract from defatted spent coffee grounds after enzymatic treatment. Monosaccharides in supernatant after acid hydrolysis.

| | Total monosaccharides/DM (%) | | | | | | | |
|---|---|---|---|---|---|---|---|---|
| | 2 h | | | | 24 h | | | |
| Enzyme treatment | Ara | Gal | Glc | Man | Ara | Gal | Glc | Man |
| GALACTANASE4 | 8 | 54 | 4 | 8 | 10 | 52 | 3 | 8 |
| Mannaway + GALACTANASE1 | 8 | 40 | 1 | 30 | 7 | 35 | 1 | 38 |
| Mannaway + GALACTANASE2 | 8 | 33 | 3 | 30 | 6 | 28 | 1 | 33 |
| Mannaway + GALACTANASE3 | 8 | 36 | 2 | 30 | 7 | 31 | 1 | 36 |
| Mannaway + GALACTANASE4 | 6 | 35 | 2 | 31 | 6 | 29 | 1 | 30 | n.d. Not determined

The difference between free and total galactose represent the content of galactooligosaccharides in the extract and likewise for the other monosaccharides.

TABLE 11

Percentage of the saccharides present as monosaccharides based on the weight of the total sugars as monosaccharides.

| | Free monosaccharides/ Total sugars (%) | |
|---|---|---|
| Enzyme treatment | 2 h | 24 h |
| No enzyme | 0 | 1 |
| Mannaway | 2 | 2 |
| GALACTANASE1 | 5 | 8 |
| GALACTANASE2 | n.d. | 2 |
| GALACTANASE3 | 1 | 2 |
| GALACTANASE4 | 24 | 23 |
| Mannaway + GALACTANASE1 | 3 | 5 |
| Mannaway + GALACTANASE2 | 2 | 3 |
| Mannaway + GALACTANASE3 | 1 | 2 |
| Mannaway + GALACTANASE4 | 13 | 13 | n.d. Not determined d) Absorbance

The absorbance at 361 nm of samples was measured after suitable dilutions of supernatants and alkalinisation by at least a 1:10 dilution in 0.2 M $Na_2CO_3$. Dividing the absorbance by the DM (g/L) gave a quality measurement relating to released colour by DM (Table 12). The galactanase released more colour per DM than Mannaway indicating a better release of flavour compounds than a Mannaway treatment. This could be due to capture of these compounds within the galactan matrix or due to their presence in melanoidin complexes released into the supernatant by the beta-1,3-galactanases. The difference in the colour release by the different enzymatic treatments were also clearly visible in the coffee extracts, easily detectable by the naked eye.

TABLE 12

Quality of extract. Absorbance of extract after alkalinisation at 361 nm per dry matter.

| | Absorbance ($A_{361}$ * L/g) | | Colour in supernatant |
|---|---|---|---|
| Enzyme treatment | 2 h | 24 h | 24 h |
| Mannaway | 0.64 | 0.50 | + |
| GALACTANASE1 | 0.77 | 0.89 | +++ |
| GALACTANASE2 | 1.05 | 0.92 | ++ |
| GALACTANASE3 | 0.92 | 0.77 | ++ |
| GALACTANASE4 | 0.85 | 0.90 | ++ |
| Mannaway + GALACTANASE1 | 0.70 | 0.71 | +++ |
| Mannaway + GALACTANASE2 | 0.72 | 0.72 | +++ |
| Mannaway + GALACTANASE3 | 0.77 | 0.78 | +++ |
| Mannaway + GALACTANASE4 | 0.68 | 0.87 | +++ | d) Molecular Weight Distribution

The molecular weight distribution of the individual extracts was analysed by size exclusion chromatography with a refractive index detector. An extract with a higher average molecular mass would contribute more to viscosity and mouth-feel than an extract with a lower average molecular mass. This parameter was therefore used as a quality parameter (Table 13). The masses were determined using a pullulan standard 342-210,000 Da as well as maltotriose, maltopentaose and maltoheptaose.

TABLE 13

Molecular weight distribution of coffee extracts. Percentages are based on the area under the curve in the respective molecular mass ranges. DP is degree of polymerization, i.e., >DP5 means the fraction of oligosaccharides having a degree of polymerization above 5. All enzymatic extracts had a peak molecular weight below 10 kDa.

| | 2 h | | | 24 h | | |
|---|---|---|---|---|---|---|
| Enzyme treatment | >DP5 | DP3-DP5 | DP1-DP3 | >DP5 | DP3-DP5 | DP1-DP3 |
| No enzyme* | 0% | 0% | 0% | 88% | 5% | 7% |
| Mannaway | 29% | 52% | 19% | 51% | 21% | 27% |
| GALACTANASE1 | 84% | 7% | 9% | 80% | 8% | 12% |
| GALACTANASE2 | 85% | 7% | 8% | 84% | 7% | 9% |
| GALACTANASE3 | 90% | 5% | 5% | 88% | 6% | 6% |
| GALACTANASE4 | 58% | 14% | 28% | 60% | 13% | 27% |
| Mannaway + GALACTANASE1 | 70% | 14% | 16% | 63% | 18% | 19% |
| Mannaway + GALACTANASE2 | 66% | 15% | 19% | 63% | 18% | 19% |

TABLE 13-continued

Molecular weight distribution of coffee extracts. Percentages are based on the area under the curve in the respective molecular mass ranges. DP is degree of polymerization, i.e., >DP5 means the fraction of oligosaccharides having a degree of polymerization above 5. All enzymatic extracts had a peak molecular weight below 10 kDa.

| | 2 h | | | 24 h | | |
|---|---|---|---|---|---|---|
| Enzyme treatment | >DP5 | DP3-DP5 | DP1-DP3 | >DP5 | DP3-DP5 | DP1-DP3 |
| Mannaway + GALACTANASE3 | 73% | 12% | 15% | 67% | 16% | 17% |
| Mannaway + GALACTANASE4 | 52% | 18% | 30% | 52% | 20% | 28% |

*Theoretically, no extra extract should be soluble from the defatted spent coffee grounds without enzyme. This is what is observed after 2 hours, but after 24 hours some sugars are still released Example 14

Enzyme Catalyzed Hydrolysis of Spent Coffee Grounds

Spent coffee grounds produced according to Example 12 at a final concentration of 10 weight % dry matter in water were incubated with Mannaway 25 L or a β-1,3-galactanase (GALACTANASE1) at a final concentration of 0.2 volume % for Mannaway 25 L and 0.05 g/L for the GALACTANASE1, for 2 and 24 h. The enzymatic reactions were carried out at 40° C. with constant mixing and were inactivated at 95° C. for 10 min.

Dry matter, carbohydrate composition, absorption at 361 nm and the molecular weight distribution of the individual extracts were measured according to Example 13. The characteristics of the extracts are summarized in Tables 14-17.

TABLE 14

Carbohydrate composition of the enzyme treated extracts of spent coffee grounds. Free monosaccharides and total monosaccharides measured after acid hydrolysis (Total sugar).

| | Free monosaccharides (g/L) | | Total sugar (g/L) | | | |
|---|---|---|---|---|---|---|
| | Gal | Man | Ara | Gal | Glc | Man |
| 2 h | | | | | | |
| No enzyme | 0 | 0 | 0.1 | 0.2 | 0 | 0.4 |
| Mannaway | 0 | 0.03 | 0.1 | 0.2 | 0 | 0.6 |
| GALACTANASE1 | 0.35 | 0 | 0.9 | 5.3 | 0 | 0.6 |
| Mannaway + GALACTANASE1 | 0.36 | 0.65 | 1.2 | 6.3 | 0.1 | 7.9 |
| 24 h | | | | | | |
| No enzyme | 0 | 0 | 0.1 | 0.2 | 0 | 0.5 |
| Mannaway | 0 | 0.16 | 0.1 | 0.4 | 0.1 | 1.8 |
| GALACTANASE1 | 0.74 | 0 | 1.4 | 7.8 | 0.1 | 0.9 |
| Mannaway + GALACTANASE1 | 0.77 | 2.08 | 2 | 9.4 | 0.1 | 17 |

TABLE 15

Characteristics of extracts. Total sugars are calculated by their weight after acid hydrolysis. Initial spent grounds concentration 100 g/L.

| | DM (g/L) | Total sugars/ DM (%) | Free monosaccharides/ DM (%) | Free monosaccharides/ total sugars (%) |
|---|---|---|---|---|
| 2 h | | | | |
| No enzyme | 2.60 | 27 | 0.0 | 0.0 |
| Mannaway | 3.26 | 28 | 0.9 | 3.3 |
| GALACTANASE1 | 9.68 | 70 | 3.6 | 5.1 |
| Mannaway + GALACTANASE1 | 19.8$^a$ | 78 | 5.1 | 6.5 |
| 24 h | | | | |
| No enzyme | 3.94 | 20 | 0.0 | 0.0 |
| Mannaway | 7.23 | 33 | 2.2 | 6.7 |
| GALACTANASE1 | 13.4 | 76 | 5.5 | 7.3 |
| Mannaway + GALACTANASE1 | 34.7$^b$ | 82 | 8.2 | 10.0 |

$^{a,b}$The synergy effect of combining Mannaway with Galactanase1 is 190% after 2 h and 200% after 24 h.

TABLE 16

Quality of extract. Absorbance of extract after alkalinisation at 361 nm per dry matter.

| | Abs$_{361}$/DM (A$_{361}$ * L/g) | |
|---|---|---|
| Enzyme treatment | 2 h | 24 h |
| Mannaway | 0.91 | 0.93 |
| GALACTANASE1 | 1.06 | 1.45 |
| Mannaway + GALACTANASE1 | 1.63 | 1.21 |

TABLE 17

Size distribuition of coffee extracts. Percentages are based on the area under the curve in the respective molecular mass ranges. All enzymatic extracts had a peak molecular weight below 10 kDa.

| | 2h | | | 24 h | | |
|---|---|---|---|---|---|---|
| Enzyme treatment | >DP5 | DP3-DP5 | DP1-DP3 | >DP5 | DP3-DP5 | DP1-DP3 |
| No enzyme | 85% | 5% | 11% | 88% | 7% | 5% |
| Mannaway | 52% | 15% | 33% | 43% | 20% | 38% |
| GALACTANASE1 | 86% | 7% | 7% | 82% | 8% | 10% |
| Mannaway + GALACTANASE1 | 60% | 16% | 23% | 45% | 16% | 39% |

Example 15

Characteristics of Coffee Made from Ground Roasted Beans and Soluble Coffee

Coffee was prepared from freshly ground "Mokka Blanding" beans (Stellini Kaffe, Odense Denmark). Soluble coffee was made by dissolving 4 g soluble coffee powder (Nescafe® Gold Blend®, golden roast) in 150 mL boiling water. Mixed coffee samples were centrifuged for 10 min at 10,000 g at 10° C. and filtered through a 0.22 μm filter before further analysis. Dry matter, saccharide composition and absorption at 361 nm was measured according to Example 13.

TABLE 18

Free monosaccharides and total sugar composition of coffee samples.

|  | Ara | Gal | Glc (g/L) | Man | Total |
|---|---|---|---|---|---|
| Coffee |  |  |  |  |  |
| Free monosaccharides | 0.01 | 0 | 0 | 0 | 0.01 |
| Total sugar | 0.3 | 0.6 | 0.2 | 0.7 | 1.8 |
| Soluble coffee |  |  |  |  |  |
| Free monosaccharides | 0.18 | 0.14 | 0.03 | 0.2 | 0.55 |
| Total sugar | 1 | 4.8 | 0.2 | 5.2 | 11.2 |

TABLE 19

Characteristics of coffee samples. Total sugars are calculated by their weight after acid hydrolysis.

|  | DM (g/L) | Total sugars/ DM (%) | Free mono-saccharides/ DM (%) | Free mono-saccharides/ Total sugars (%) |
|---|---|---|---|---|
| Coffee | 9 | 20.0 | 0.1 | 0.6 |
| Soluble coffee | 25 | 44.8 | 2.2 | 4.9 |

TABLE 20

Quality of extract. Absorbance of extract after alkalinisation at 361 nm and per dry matter

|  | $Abs_{361}$ | $Abs_{361}/DM$ ($Abs_{361}$ * L/g) |
|---|---|---|
| Coffee | 61 | 6.7 |
| Soluble coffee | 99 | 3.9 |

The invention claimed is:

1. A method for producing a coffee extract which comprises at least 20% total galactose based on the total weight of soluble coffee solids, comprising the steps:
    (a) adding water, an endo-β-1,3-galactanase (EC 3.2.1.181), and a β-mannanase to roasted and ground coffee beans, wherein the endo-β-1,3-galactanase is added at a concentration of at least 0.001 g/kg coffee beans and a β-mannanase is added in an amount to produce an increased yield of solubilised coffee solids in the coffee extract which is greater than additive as compared to the increased yield of solubilised coffee solids obtained by incubation with each enzyme alone;
    (b) incubating to make an aqueous coffee extract; and
    (c) separating the coffee extract from the coffee beans;
    wherein the coffee extract comprises at least 20% total galactose, based on the total weight of soluble coffee solids.

2. The method of claim 1, wherein the endo-β-1,3-galactanase is added at a concentration of 0.001-0.5 g enzymes protein/kg coffee beans.

3. The method of claim 1, wherein the endo-β-1,3-galactanase is a β-1,3-galactanase of the GH16 family.

4. The method of claim 1, wherein the endo-β-1,3-galactanase has an amino acid sequence which has at least 90% identity to the mature sequence of any of SEQ ID Nos: 2, 4 or 8.

5. The method of claim 1, wherein the roast and ground coffee beans have been partially extracted.

6. The method of claim 3, wherein the endo-β-1,3-galactanase is a fungal δ-1,3-galactanase.

7. The method of claim 1, wherein the endo-β-1,3-galactanase is added at a concentration of at least 0.005 g enzyme protein/kg coffee beans.

8. The method of claim 1, wherein the endo-β-1,3-galactanase is added at a concentration of 0.005-0.2 g enzyme protein/kg coffee beans.

9. The method of claim 1, wherein the coffee extract obtained by the method has a weight ratio of total galactose to total arabinose of more than 3:1.

10. The method of claim 1, wherein the coffee extract obtained by the method has a weight ratio of total galactose to total arabinose of more than 5:1.

* * * * *

SEQUENCE LISTING

```
<160> NUMBER OF SEQ ID NOS: 15

<210> SEQ ID NO 1
<211> LENGTH: 771
<212> TYPE: DNA
<213> ORGANISM: Artificial Sequence
<220> FEATURE:
<223> OTHER INFORMATION: Synthetic construct
<220> FEATURE:
<221> NAME/KEY: CDS
<222> LOCATION: (1)..(768)

<400> SEQUENCE: 1 atg att tcc gtc gct ttg gtc cca ctc ttc atc gct gtg ctt gcc agc        48
Met Ile Ser Val Ala Leu Val Pro Leu Phe Ile Ala Val Leu Ala Ser
1               5                   10                  15 gcg acg tcg agc gtc gtc ctc ccg acg aac tcg ttc agc tcg tac agc        96
Ala Thr Ser Ser Val Val Leu Pro Thr Asn Ser Phe Ser Ser Tyr Ser
            20                  25                  30 gcc ttt gag cag cac tgg aac tac ctc tac cct tgg ggc tcg gac cac       144
Ala Phe Glu Gln His Trp Asn Tyr Leu Tyr Pro Trp Gly Ser Asp His
        35                  40                  45 aac ggc tcc ggg cgc atg gtg ggc agc tcg tcg aac cac acg tac atc       192
Asn Gly Ser Gly Arg Met Val Gly Ser Ser Ser Asn His Thr Tyr Ile
    50                  55                  60 agc gtc gcg gac aac gtt ctc acg ctc acc tcg aag ccc gtc tcc ggg       240
Ser Val Ala Asp Asn Val Leu Thr Leu Thr Ser Lys Pro Val Ser Gly
65                  70                  75                  80 cag cct ccg agc acc tcc aac ccg cac ccg gcc atc cat tac ttc tct       288
Gln Pro Pro Ser Thr Ser Asn Pro His Pro Ala Ile His Tyr Phe Ser
                85                  90                  95 ggc act gtc cat gcg aag caa cag gtc aag gtc gac gga agt agc gtc       336
Gly Thr Val His Ala Lys Gln Gln Val Lys Val Asp Gly Ser Ser Val
            100                 105                 110 acg ggg ttc gac atc cag gga gag ttc att gct ccg act gca aaa ggc       384
Thr Gly Phe Asp Ile Gln Gly Glu Phe Ile Ala Pro Thr Ala Lys Gly
        115                 120                 125 acg tgg cct gcg ttc tgg ctt act gcg gtg aat gga tgg cct ccg gag       432
Thr Trp Pro Ala Phe Trp Leu Thr Ala Val Asn Gly Trp Pro Pro Glu
    130                 135                 140
```

```
agc gac att ggt gaa tgg aag ggc acc cag gaa aac tgg ttc aat acc      480
Ser Asp Ile Gly Glu Trp Lys Gly Thr Gln Glu Asn Trp Phe Asn Thr
145                 150                 155                 160 ttc aac act tcc tca tca gtc gcg acg aag cgc gtc gcc tgg ccc acg      528
Phe Asn Thr Ser Ser Ser Val Ala Thr Lys Arg Val Ala Trp Pro Thr
                165                 170                 175 gac ggc cag ttc cat tcc ctg aag gcc gag ctg cgc acg atc tcg ggc      576
Asp Gly Gln Phe His Ser Leu Lys Ala Glu Leu Arg Thr Ile Ser Gly
            180                 185                 190 aac acg aag gac ctc tcg atc aag tac tac ttc gac gga acg ctg cag      624
Asn Thr Lys Asp Leu Ser Ile Lys Tyr Tyr Phe Asp Gly Thr Leu Gln
        195                 200                 205 gcg act cac acg gca gct aac ttc cgc aac gcc gct atg tgg ttg att      672
Ala Thr His Thr Ala Ala Asn Phe Arg Asn Ala Ala Met Trp Leu Ile
    210                 215                 220 gtc gac ctt cag atg gag gga agc tcg ggc tct ccg ggc cca gct ggc      720
Val Asp Leu Gln Met Glu Gly Ser Ser Gly Ser Pro Gly Pro Ala Gly
225                 230                 235                 240 ggc acg acg ttc caa atc agg aac gtc cag ttg acg aag tat acg ccg      768
Gly Thr Thr Phe Gln Ile Arg Asn Val Gln Leu Thr Lys Tyr Thr Pro
                245                 250                 255 tga                                                                  771

<210> SEQ ID NO 2
<211> LENGTH: 256
<212> TYPE: PRT
<213> ORGANISM: Artificial Sequence
<220> FEATURE:
<223> OTHER INFORMATION: Synthetic Construct

<400> SEQUENCE: 2

Met Ile Ser Val Ala Leu Val Pro Leu Phe Ile Ala Val Leu Ala Ser
1               5                   10                  15

Ala Thr Ser Ser Val Val Leu Pro Thr Asn Ser Phe Ser Ser Tyr Ser
            20                  25                  30

Ala Phe Glu Gln His Trp Asn Tyr Leu Tyr Pro Trp Gly Ser Asp His
        35                  40                  45

Asn Gly Ser Gly Arg Met Val Gly Ser Ser Ser Asn His Thr Tyr Ile
    50                  55                  60

Ser Val Ala Asp Asn Val Leu Thr Leu Thr Ser Lys Pro Val Ser Gly
65                  70                  75                  80

Gln Pro Pro Ser Thr Ser Asn Pro His Pro Ala Ile His Tyr Phe Ser
                85                  90                  95

Gly Thr Val His Ala Lys Gln Gln Val Lys Val Asp Gly Ser Ser Val
            100                 105                 110

Thr Gly Phe Asp Ile Gln Gly Glu Phe Ile Ala Pro Thr Ala Lys Gly
        115                 120                 125

Thr Trp Pro Ala Phe Trp Leu Thr Ala Val Asn Gly Trp Pro Pro Glu
    130                 135                 140

Ser Asp Ile Gly Glu Trp Lys Gly Thr Gln Glu Asn Trp Phe Asn Thr
145                 150                 155                 160

Phe Asn Thr Ser Ser Ser Val Ala Thr Lys Arg Val Ala Trp Pro Thr
                165                 170                 175

Asp Gly Gln Phe His Ser Leu Lys Ala Glu Leu Arg Thr Ile Ser Gly
            180                 185                 190

Asn Thr Lys Asp Leu Ser Ile Lys Tyr Tyr Phe Asp Gly Thr Leu Gln
        195                 200                 205
```

```
Ala Thr His Thr Ala Ala Asn Phe Arg Asn Ala Ala Met Trp Leu Ile
    210                 215                 220

Val Asp Leu Gln Met Glu Gly Ser Ser Gly Ser Pro Gly Pro Ala Gly
225                 230                 235                 240

Gly Thr Thr Phe Gln Ile Arg Asn Val Gln Leu Thr Lys Tyr Thr Pro
                245                 250                 255

<210> SEQ ID NO 3
<211> LENGTH: 777
<212> TYPE: DNA
<213> ORGANISM: Artificial Sequence
<220> FEATURE:
<223> OTHER INFORMATION: Synthetic construct
<220> FEATURE:
<221> NAME/KEY: CDS
<222> LOCATION: (1)..(774)

<400> SEQUENCE: 3
```

| | | | | | | | | | | | | | | | | |
|---|---|---|---|---|---|---|---|---|---|---|---|---|---|---|---|---|
| atg | ttt | aat | tct | ata | ccc | cat | ttc | ctg | cta | atg | acc | tct | ggg | gtc | gga | 48 |
| Met | Phe | Asn | Ser | Ile | Pro | His | Phe | Leu | Leu | Met | Thr | Ser | Gly | Val | Gly | |
| 1 | | | | 5 | | | | | 10 | | | | | 15 | | |

```
att gcg ttg atg cca caa gtg atg gca gtc agg acc atg ata cca tgc    96
Ile Ala Leu Met Pro Gln Val Met Ala Val Arg Thr Met Ile Pro Cys
             20                  25                  30 acc agc ttc gac aac cag tcc aac ttc gac gca gac tgg aat tac aac   144
Thr Ser Phe Asp Asn Gln Ser Asn Phe Asp Ala Asp Trp Asn Tyr Asn
         35                  40                  45 tac ccc tgg gga acc gac cac aac ggc gcg cgt atg gat ggt gcc       192
Tyr Pro Trp Gly Thr Asp His Asn Gly Ala Ala Arg Met Asp Gly Ala
     50                  55                  60 aac gcg gtc cgg ttg gcg agc aga ggt gac cgt aca ctt gtc att act   240
Asn Ala Val Arg Leu Ala Ser Arg Gly Asp Arg Thr Leu Val Ile Thr
65                  70                  75                  80 gca cgc cgt gcc gaa ggc ctg ccg cct gcc act cac gga ggc cag cag   288
Ala Arg Arg Ala Glu Gly Leu Pro Pro Ala Thr His Gly Gly Gln Gln
                 85                  90                  95 att cct atc agg tat ctg tct ggg gcc atc cac gcc aaa gaa cag ttt   336
Ile Pro Ile Arg Tyr Leu Ser Gly Ala Ile His Ala Lys Glu Gln Phe
            100                 105                 110 act gtc cgg cca aac ggc ggc tac gat ttc aca gga gag ttc aaa gcc   384
Thr Val Arg Pro Asn Gly Gly Tyr Asp Phe Thr Gly Glu Phe Lys Ala
        115                 120                 125 aca aca acc aag ggt acc tgg cca gcc ttc tgg ctc aca gga gtg gac   432
Thr Thr Thr Lys Gly Thr Trp Pro Ala Phe Trp Leu Thr Gly Val Asp
    130                 135                 140 agt tgg cca ccg gag att gac atg gca gaa tgg aaa ggt agc ggg aaa   480
Ser Trp Pro Pro Glu Ile Asp Met Ala Glu Trp Lys Gly Ser Gly Lys
145                 150                 155                 160 atc agc ttc aac acg ttc aac acg tcg agc gaa gtc gtg tcg cga gac   528
Ile Ser Phe Asn Thr Phe Asn Thr Ser Ser Glu Val Val Ser Arg Asp
                165                 170                 175 gtg gat tac cct gcg cct gac cag ttc cat agc atc aag tgc gaa gtg   576
Val Asp Tyr Pro Ala Pro Asp Gln Phe His Ser Ile Lys Cys Glu Val
            180                 185                 190 aga gac gaa ggg cag gat gtc cgc gcc aat ttc tat atg gat ggc aac   624
Arg Asp Glu Gly Gln Asp Val Arg Ala Asn Phe Tyr Met Asp Gly Asn
        195                 200                 205 ctg ctt acc act cag atc gga aaa gga tac gtc ggg aaa cca ctc ttc   672
Leu Leu Thr Thr Gln Ile Gly Lys Gly Tyr Val Gly Lys Pro Leu Phe
    210                 215                 220 ttg att atc aac ttg cag atg gag gga tct tcg ggc acc ccg ggc ccc   720
Leu Ile Ile Asn Leu Gln Met Glu Gly Ser Ser Gly Thr Pro Gly Pro
```

```
Leu Ile Ile Asn Leu Gln Met Glu Gly Ser Ser Gly Thr Pro Gly Pro
225                 230                 235                 240 gag tca gat acc gaa tac gcc ata cga aac ctg gag gtt ctt tcc tat    768
Glu Ser Asp Thr Glu Tyr Ala Ile Arg Asn Leu Glu Val Leu Ser Tyr
                245                 250                 255 aac ccg tga                                                         777
Asn Pro
```

<210> SEQ ID NO 4
<211> LENGTH: 258
<212> TYPE: PRT
<213> ORGANISM: Artificial Sequence
<220> FEATURE:
<223> OTHER INFORMATION: Synthetic Construct

<400> SEQUENCE: 4

```
Met Phe Asn Ser Ile Pro His Phe Leu Leu Met Thr Ser Gly Val Gly
1               5                   10                  15

Ile Ala Leu Met Pro Gln Val Met Ala Val Arg Thr Met Ile Pro Cys
                20                  25                  30

Thr Ser Phe Asp Asn Gln Ser Asn Phe Asp Ala Asp Trp Asn Tyr Asn
            35                  40                  45

Tyr Pro Trp Gly Thr Asp His Asn Gly Ala Ala Arg Met Asp Gly Ala
        50                  55                  60

Asn Ala Val Arg Leu Ala Ser Arg Gly Asp Arg Thr Leu Val Ile Thr
65                  70                  75                  80

Ala Arg Arg Ala Glu Gly Leu Pro Pro Ala Thr His Gly Gly Gln Gln
                85                  90                  95

Ile Pro Ile Arg Tyr Leu Ser Gly Ala Ile His Ala Lys Glu Gln Phe
            100                 105                 110

Thr Val Arg Pro Asn Gly Gly Tyr Asp Phe Thr Gly Glu Phe Lys Ala
        115                 120                 125

Thr Thr Thr Lys Gly Thr Trp Pro Ala Phe Trp Leu Thr Gly Val Asp
130                 135                 140

Ser Trp Pro Pro Glu Ile Asp Met Ala Glu Trp Lys Gly Ser Gly Lys
145                 150                 155                 160

Ile Ser Phe Asn Thr Phe Asn Thr Ser Ser Glu Val Val Ser Arg Asp
                165                 170                 175

Val Asp Tyr Pro Ala Pro Asp Gln Phe His Ser Ile Lys Cys Glu Val
            180                 185                 190

Arg Asp Glu Gly Gln Asp Val Arg Ala Asn Phe Tyr Met Asp Gly Asn
        195                 200                 205

Leu Leu Thr Thr Gln Ile Gly Lys Gly Tyr Val Gly Lys Pro Leu Phe
210                 215                 220

Leu Ile Ile Asn Leu Gln Met Glu Gly Ser Ser Gly Thr Pro Gly Pro
225                 230                 235                 240

Glu Ser Asp Thr Glu Tyr Ala Ile Arg Asn Leu Glu Val Leu Ser Tyr
                245                 250                 255

Asn Pro
```

<210> SEQ ID NO 5
<211> LENGTH: 43
<212> TYPE: DNA
<213> ORGANISM: Artificial Sequence
<220> FEATURE:
<223> OTHER INFORMATION: Synthetic construct

<400> SEQUENCE: 5
acacaactgg ggatccacca tgaggaggtc cttccaacaa ccc                43

<210> SEQ ID NO 6
<211> LENGTH: 41
<212> TYPE: DNA
<213> ORGANISM: Artificial Sequence
<220> FEATURE:
<223> OTHER INFORMATION: Synthetic construct

<400> SEQUENCE: 6
ccctctagat ctcgagtgga catcttgaag ggacaactcc t                  41

<210> SEQ ID NO 7
<211> LENGTH: 1061
<212> TYPE: DNA
<213> ORGANISM: Neurospora crassa
<220> FEATURE:
<221> NAME/KEY: exon
<222> LOCATION: (1)..(710)
<220> FEATURE:
<221> NAME/KEY: CDS
<222> LOCATION: (1)..(710)
<220> FEATURE:
<221> NAME/KEY: Intron
<222> LOCATION: (711)..(840)
<220> FEATURE:
<221> NAME/KEY: exon
<222> LOCATION: (841)..(893)
<220> FEATURE:
<221> NAME/KEY: CDS
<222> LOCATION: (841)..(893)
<220> FEATURE:
<221> NAME/KEY: Intron
<222> LOCATION: (894)..(990)
<220> FEATURE:
<221> NAME/KEY: exon
<222> LOCATION: (991)..(1025)
<220> FEATURE:
<221> NAME/KEY: CDS
<222> LOCATION: (991)..(1022)
<220> FEATURE:
<221> NAME/KEY: 3'UTR
<222> LOCATION: (1026)..(1061)

<400> SEQUENCE: 7

```
atg agg agg tcc ttc caa caa ccc ctt ccc ctt ctc ctc caa acc atc     48
Met Arg Arg Ser Phe Gln Gln Pro Leu Pro Leu Leu Leu Gln Thr Ile
1               5                   10                  15 acc atc ctc tgc ctc ttc cca tct acc ctc gcc tca tcc aag acc ctc     96
Thr Ile Leu Cys Leu Phe Pro Ser Thr Leu Ala Ser Ser Lys Thr Leu
            20                  25                  30 cta atc cct tcc aca tcc ttc aac tcc acc acc acc ttc aac acc tac    144
Leu Ile Pro Ser Thr Ser Phe Asn Ser Thr Thr Thr Phe Asn Thr Tyr
        35                  40                  45 tgg tcc ttc aat tac ccc tgg ggc acc gac cac aat ggc gcc gcg cgc    192
Trp Ser Phe Asn Tyr Pro Trp Gly Thr Asp His Asn Gly Ala Ala Arg
    50                  55                  60 atg tcc cct tcc caa gtc tcc ata gcc ccc tct gct gac ggc acc tca    240
Met Ser Pro Ser Gln Val Ser Ile Ala Pro Ser Ala Asp Gly Thr Ser
65                  70                  75                  80 agc acc ctc act cta acc gcc cac cgc gtc acc ggc caa aaa ccc gct    288
Ser Thr Leu Thr Leu Thr Ala His Arg Val Thr Gly Gln Lys Pro Ala
                85                  90                  95 acc cac ggc ggc aaa cag atc ccc atc aag tac cta tcc ggc gcc atc    336
Thr His Gly Gly Lys Gln Ile Pro Ile Lys Tyr Leu Ser Gly Ala Ile
            100                 105                 110 cac gcc aag cag cac ttc acc att act tct tct tct tct ggt gct ggt    384
```

```
His Ala Lys Gln His Phe Thr Ile Thr Ser Ser Ser Gly Ala Gly
            115                 120                 125 gca gtg tca ggc tac gat ttc tca gcc gag ttc cgc gcc ccc gtt gcg      432
Ala Val Ser Gly Tyr Asp Phe Ser Ala Glu Phe Arg Ala Pro Val Ala
130                 135                 140 aag ggg acc tgg cct gcg ttt tgg ttg acg gcc gtc aat ggg tgg ccg      480
Lys Gly Thr Trp Pro Ala Phe Trp Leu Thr Ala Val Asn Gly Trp Pro
145                 150                 155                 160 ccc gag att gat atg gcg gag tgg aag ggg agc ggc aag att agc ttt      528
Pro Glu Ile Asp Met Ala Glu Trp Lys Gly Ser Gly Lys Ile Ser Phe
                165                 170                 175 aac acg ttc aat act agt agt cag gtc atg gct cgg gat gtg gtt tat      576
Asn Thr Phe Asn Thr Ser Ser Gln Val Met Ala Arg Asp Val Val Tyr
            180                 185                 190 ggc ccg aac ggg agt gag aag gag tgg cat agg gtt gtg tgt gag atc      624
Gly Pro Asn Gly Ser Glu Lys Glu Trp His Arg Val Val Cys Glu Ile
        195                 200                 205 agg agg gat gga agg aat ggt gga aag gat gtg gag gtg agg ttt cgg      672
Arg Arg Asp Gly Arg Asn Gly Gly Lys Asp Val Glu Val Arg Phe Arg
210                 215                 220 atg gat ggg cag cta gtg gta acg cag tgg ggg aag gg gtatgttggg        720
Met Asp Gly Gln Leu Val Val Thr Gln Trp Gly Lys Gly
225                 230                 235 cagccacttt atttgtgagt ttaaaccttt ttttttcct ttttttttct tcttcttctt     780
tcgttgtcgg ggtgaggttt ttcgcgttgt cggttgctaa ctggaagggt gatattgcag    840 g att atc aat ctc cag atg gaa ggg tcg tcg ggt tca cct ggt cct gaa    889
  Ile Ile Asn Leu Gln Met Glu Gly Ser Ser Gly Ser Pro Gly Pro Glu
      240                 245                 250 gcg g gtaagtcaac tataggtctc ttcgttttgg tgatggaaga acctgatcgt         943
Ala ctcagccggt ccatttgctg acagtgatac agacactttg tatcaag tc cga aat       998
                                                        Val Arg Asn
                                                                255 ctt gag gtc tgg agc tat ggt gac tga gccgtgagca gaggagttgt           1045
Leu Glu Val Trp Ser Tyr Gly Asp
        260                 265 cccttcaaga tgtcca                                                   1061

<210> SEQ ID NO 8
<211> LENGTH: 265
<212> TYPE: PRT
<213> ORGANISM: Neurospora crassa

<400> SEQUENCE: 8

Met Arg Arg Ser Phe Gln Gln Pro Leu Pro Leu Leu Gln Thr Ile
1               5                   10                  15

Thr Ile Leu Cys Leu Phe Pro Ser Thr Leu Ala Ser Ser Lys Thr Leu
            20                  25                  30

Leu Ile Pro Ser Thr Ser Phe Asn Ser Thr Thr Phe Asn Thr Tyr
        35                  40                  45

Trp Ser Phe Asn Tyr Pro Trp Gly Thr Asp His Asn Gly Ala Ala Arg
    50                  55                  60

Met Ser Pro Ser Gln Val Ser Ile Ala Pro Ala Asp Gly Thr Ser
65                  70                  75                  80

Ser Thr Leu Thr Leu Thr Ala His Arg Val Thr Gly Gln Lys Pro Ala
                85                  90                  95

Thr His Gly Gly Lys Gln Ile Pro Ile Lys Tyr Leu Ser Gly Ala Ile
```

```
                100                 105                 110
His Ala Lys Gln His Phe Thr Ile Thr Ser Ser Ser Gly Ala Gly
            115                 120                 125

Ala Val Ser Gly Tyr Asp Phe Ser Ala Glu Phe Arg Ala Pro Val Ala
130                 135                 140

Lys Gly Thr Trp Pro Ala Phe Trp Leu Thr Ala Val Asn Gly Trp Pro
145                 150                 155                 160

Pro Glu Ile Asp Met Ala Glu Trp Lys Gly Ser Gly Lys Ile Ser Phe
                165                 170                 175

Asn Thr Phe Asn Thr Ser Ser Gln Val Met Ala Arg Asp Val Val Tyr
            180                 185                 190

Gly Pro Asn Gly Ser Glu Lys Glu Trp His Arg Val Cys Glu Ile
            195                 200                 205

Arg Arg Asp Gly Arg Asn Gly Gly Lys Asp Val Glu Val Arg Phe Arg
        210                 215                 220

Met Asp Gly Gln Leu Val Val Thr Gln Trp Gly Lys Gly Ile Ile Asn
225                 230                 235                 240

Leu Gln Met Glu Gly Ser Ser Gly Ser Pro Gly Pro Glu Ala Val Arg
                245                 250                 255

Asn Leu Glu Val Trp Ser Tyr Gly Asp
            260                 265

<210> SEQ ID NO 9
<211> LENGTH: 1347
<212> TYPE: DNA
<213> ORGANISM: Artificial Sequence
<220> FEATURE:
<223> OTHER INFORMATION: Synthetic construct
<220> FEATURE:
<221> NAME/KEY: CDS
<222> LOCATION: (1)..(1344)

<400> SEQUENCE: 9 atg ttg tgg ttg cgc aag gtg atc cct gtt ttc ctc tct ctg gtc gtt      48
Met Leu Trp Leu Arg Lys Val Ile Pro Val Phe Leu Ser Leu Val Val
1               5                   10                  15 gcg gcc cgc gcc gag aca cag atc gtc tct ggt gct gct tgg aca gac      96
Ala Ala Arg Ala Glu Thr Gln Ile Val Ser Gly Ala Ala Trp Thr Asp
                20                  25                  30 aca agc gga aac gtc att cag gcc cat ggc gct gga atc ttg aag gtc     144
Thr Ser Gly Asn Val Ile Gln Ala His Gly Ala Gly Ile Leu Lys Val
        35                  40                  45 gga agc acg ttt tac tgg ttc ggt gaa gac aag acg gag aac agt gcc     192
Gly Ser Thr Phe Tyr Trp Phe Gly Glu Asp Lys Thr Glu Asn Ser Ala
    50                  55                  60 ttg ttc cac gca gtg tcg tgc tat aca tct acg gac ctg acg aac tgg     240
Leu Phe His Ala Val Ser Cys Tyr Thr Ser Thr Asp Leu Thr Asn Trp
65                  70                  75                  80 act cgt caa agc aat gcg ctt tct ccg gtc gcc aac acc atg att tcc     288
Thr Arg Gln Ser Asn Ala Leu Ser Pro Val Ala Asn Thr Met Ile Ser
                85                  90                  95 tct aac aac atc gtt gag cgt ccc aaa gtt tta ttc aac aag aag aat     336
Ser Asn Asn Ile Val Glu Arg Pro Lys Val Leu Phe Asn Lys Lys Asn
            100                 105                 110 caa gaa tac gtg atg tgg ttc cat tct gat agt tcc aac tat gga gct     384
Gln Glu Tyr Val Met Trp Phe His Ser Asp Ser Ser Asn Tyr Gly Ala
        115                 120                 125 gcc atg gtc ggt gtc gca act gcg aaa act ccc tgc ggc ccc tat aca     432
Ala Met Val Gly Val Ala Thr Ala Lys Thr Pro Cys Gly Pro Tyr Thr
```

```
                  130                 135                 140
ttc aaa ggc agc ttc aaa cct ctc ggc gca gat tct cgc gat gaa ggg      480
Phe Lys Gly Ser Phe Lys Pro Leu Gly Ala Asp Ser Arg Asp Glu Gly
145                 150                 155                 160 ctg ttt cag gat gac gac tcc gca caa acc gcc tac ctt ctc tat gcc      528
Leu Phe Gln Asp Asp Asp Ser Ala Gln Thr Ala Tyr Leu Leu Tyr Ala
                        165                 170                 175 tcc gat aac aac cag aac ttc aag ata tca agg ttg gat gac aac tat      576
Ser Asp Asn Asn Gln Asn Phe Lys Ile Ser Arg Leu Asp Asp Asn Tyr
                180                 185                 190 tac aat gtg act gct cag gct agc gtt ttg acc ggt gcc aca ctt gaa      624
Tyr Asn Val Thr Ala Gln Ala Ser Val Leu Thr Gly Ala Thr Leu Glu
            195                 200                 205 gca ccg ggc att gta aag cac agc gga aaa tac ttc cta atc gcc tcg      672
Ala Pro Gly Ile Val Lys His Ser Gly Lys Tyr Phe Leu Ile Ala Ser
        210                 215                 220 cac acc agc gga tgg gct ccg aac cca aac aag ttc ttc tca gca tct      720
His Thr Ser Gly Trp Ala Pro Asn Pro Asn Lys Phe Phe Ser Ala Ser
225                 230                 235                 240 tcc ttg tcc ggc ccg tgg tcg tct caa caa gat atc acc acc gcg tcc      768
Ser Leu Ser Gly Pro Trp Ser Ser Gln Gln Asp Ile Thr Thr Ala Ser
                        245                 250                 255 aca cgc acc tgg tac tcg caa aac gca ttc gac ttg cct ctc ggt aat      816
Thr Arg Thr Trp Tyr Ser Gln Asn Ala Phe Asp Leu Pro Leu Gly Asn
                260                 265                 270 aat gcg atc tac atg gga gat agg tgg agg ccc agc tta ctt gga agc      864
Asn Ala Ile Tyr Met Gly Asp Arg Trp Arg Pro Ser Leu Leu Gly Ser
            275                 280                 285 agc cgg tac atc tgg tat cct atc gat ttc tcc agc ggg tcg ccg caa      912
Ser Arg Tyr Ile Trp Tyr Pro Ile Asp Phe Ser Ser Gly Ser Pro Gln
        290                 295                 300 ctc gtg cat gcc gat gtg tgg tcg gtg aac ccg tct gcc ggc acg tat      960
Leu Val His Ala Asp Val Trp Ser Val Asn Pro Ser Ala Gly Thr Tyr
305                 310                 315                 320 act gtt gct caa gga acc act tac gaa gct gag aag ggt aca ctc ggc     1008
Thr Val Ala Gln Gly Thr Thr Tyr Glu Ala Glu Lys Gly Thr Leu Gly
                        325                 330                 335 ggg tct tcc aag ctc ttg tcc aat tcg ggg ttc tct ggg ggc agc gca     1056
Gly Ser Ser Lys Leu Leu Ser Asn Ser Gly Phe Ser Gly Gly Ser Ala
                340                 345                 350 gta ggt tac ctc ggt cat ggt ggc act gtg acg atc aac aac gtt caa     1104
Val Gly Tyr Leu Gly His Gly Gly Thr Val Thr Ile Asn Asn Val Gln
            355                 360                 365 ggc aat gga gga gcg cac tgg gtt gcg atc tat ttt gcc aat ggc gac     1152
Gly Asn Gly Gly Ala His Trp Val Ala Ile Tyr Phe Ala Asn Gly Asp
        370                 375                 380 tcc aca tat agg aat gtc acc gtc agc gta aat gga ggc tcc tct gtt     1200
Ser Thr Tyr Arg Asn Val Thr Val Ser Val Asn Gly Gly Ser Ser Val
385                 390                 395                 400 ctc gtc gac cag cca gac tct gga gga gga ggc gta gtc att agt gta     1248
Leu Val Asp Gln Pro Asp Ser Gly Gly Gly Gly Val Val Ile Ser Val
                        405                 410                 415 cct gtc aaa gtg aac ctg aat aat ggc gca aac tcg atc acc ttt ggc     1296
Pro Val Lys Val Asn Leu Asn Asn Gly Ala Asn Ser Ile Thr Phe Gly
                420                 425                 430 tcc gga caa tcc aat tac gct gcc gac ctt gac aag att atc gtc tac     1344
Ser Gly Gln Ser Asn Tyr Ala Ala Asp Leu Asp Lys Ile Ile Val Tyr
            435                 440                 445 tga                                                                 1347
```

<210> SEQ ID NO 10
<211> LENGTH: 448
<212> TYPE: PRT
<213> ORGANISM: Artificial Sequence
<220> FEATURE:
<223> OTHER INFORMATION: Synthetic Construct

<400> SEQUENCE: 10

```
Met Leu Trp Leu Arg Lys Val Ile Pro Val Phe Leu Ser Leu Val Val
1               5                   10                  15

Ala Ala Arg Ala Glu Thr Gln Ile Val Ser Gly Ala Ala Trp Thr Asp
            20                  25                  30

Thr Ser Gly Asn Val Ile Gln Ala His Gly Ala Gly Ile Leu Lys Val
        35                  40                  45

Gly Ser Thr Phe Tyr Trp Phe Gly Glu Asp Lys Thr Glu Asn Ser Ala
    50                  55                  60

Leu Phe His Ala Val Ser Cys Tyr Thr Ser Thr Asp Leu Thr Asn Trp
65                  70                  75                  80

Thr Arg Gln Ser Asn Ala Leu Ser Pro Val Ala Asn Thr Met Ile Ser
                85                  90                  95

Ser Asn Asn Ile Val Glu Arg Pro Lys Val Leu Phe Asn Lys Lys Asn
            100                 105                 110

Gln Glu Tyr Val Met Trp Phe His Ser Asp Ser Ser Asn Tyr Gly Ala
        115                 120                 125

Ala Met Val Gly Val Ala Thr Ala Lys Thr Pro Cys Gly Pro Tyr Thr
    130                 135                 140

Phe Lys Gly Ser Phe Lys Pro Leu Gly Ala Asp Ser Arg Asp Glu Gly
145                 150                 155                 160

Leu Phe Gln Asp Asp Ser Ala Gln Thr Ala Tyr Leu Leu Tyr Ala
                165                 170                 175

Ser Asp Asn Asn Gln Asn Phe Lys Ile Ser Arg Leu Asp Asp Asn Tyr
            180                 185                 190

Tyr Asn Val Thr Ala Gln Ala Ser Val Leu Thr Gly Ala Thr Leu Glu
        195                 200                 205

Ala Pro Gly Ile Val Lys His Ser Gly Lys Tyr Phe Leu Ile Ala Ser
    210                 215                 220

His Thr Ser Gly Trp Ala Pro Asn Pro Asn Lys Phe Phe Ser Ala Ser
225                 230                 235                 240

Ser Leu Ser Gly Pro Trp Ser Ser Gln Gln Asp Ile Thr Thr Ala Ser
                245                 250                 255

Thr Arg Thr Trp Tyr Ser Gln Asn Ala Phe Asp Leu Pro Leu Gly Asn
            260                 265                 270

Asn Ala Ile Tyr Met Gly Asp Arg Trp Arg Pro Ser Leu Leu Gly Ser
        275                 280                 285

Ser Arg Tyr Ile Trp Tyr Pro Ile Asp Phe Ser Ser Gly Ser Pro Gln
    290                 295                 300

Leu Val His Ala Asp Val Trp Ser Val Asn Pro Ser Ala Gly Thr Tyr
305                 310                 315                 320

Thr Val Ala Gln Gly Thr Thr Tyr Glu Ala Glu Lys Gly Thr Leu Gly
                325                 330                 335

Gly Ser Ser Lys Leu Leu Ser Asn Ser Gly Phe Ser Gly Gly Ser Ala
            340                 345                 350

Val Gly Tyr Leu Gly His Gly Gly Thr Val Thr Ile Asn Asn Val Gln
        355                 360                 365
```

```
Gly Asn Gly Gly Ala His Trp Val Ala Ile Tyr Phe Ala Asn Gly Asp
        370                 375                 380

Ser Thr Tyr Arg Asn Val Thr Val Ser Val Asn Gly Gly Ser Ser Val
385                 390                 395                 400

Leu Val Asp Gln Pro Asp Ser Gly Gly Gly Val Val Ile Ser Val
                405                 410                 415

Pro Val Lys Val Asn Leu Asn Asn Gly Ala Asn Ser Ile Thr Phe Gly
                420                 425                 430

Ser Gly Gln Ser Asn Tyr Ala Ala Asp Leu Asp Lys Ile Ile Val Tyr
            435                 440                 445

<210> SEQ ID NO 11
<211> LENGTH: 1224
<212> TYPE: DNA
<213> ORGANISM: Artificial Sequence
<220> FEATURE:
<223> OTHER INFORMATION: Synthetic construct
<220> FEATURE:
<221> NAME/KEY: CDS
<222> LOCATION: (1)..(1224)

<400> SEQUENCE: 11
```

| | | | | | | | | | | | | | | | | |
|---|---|---|---|---|---|---|---|---|---|---|---|---|---|---|---|---|
| atg | agg | ttg | cag | aag | gat | ttc | gat | cga | gtc | atg | ggc | att | atc | ttg | atg | 48 |
| Met | Arg | Leu | Gln | Lys | Asp | Phe | Asp | Arg | Val | Met | Gly | Ile | Ile | Leu | Met | |
| 1 | | | | 5 | | | | | 10 | | | | | 15 | | |
| att | ctc | att | ctc | gca | atc | ccc | tcc | ttg | cag | atc | tgt | aac | aag | tcg | tac | 96 |
| Ile | Leu | Ile | Leu | Ala | Ile | Pro | Ser | Leu | Gln | Ile | Cys | Asn | Lys | Ser | Tyr | |
| | | | 20 | | | | | 25 | | | | | 30 | | | |
| act | gag | ggc | gac | ccg | gtc | atc | atc | aac | ccg | gtc | cct | ggc | ctc | ccc | gtc | 144 |
| Thr | Glu | Gly | Asp | Pro | Val | Ile | Ile | Asn | Pro | Val | Pro | Gly | Leu | Pro | Val | |
| | | 35 | | | | | 40 | | | | | 45 | | | | |
| gac | ttc | att | cga | ggt | gtg | gat | gca | tcg | gaa | gca | ccc | tgg | atc | atc | gag | 192 |
| Asp | Phe | Ile | Arg | Gly | Val | Asp | Ala | Ser | Glu | Ala | Pro | Trp | Ile | Ile | Glu | |
| | 50 | | | | | 55 | | | | | 60 | | | | | |
| ttg | ggt | ggc | aag | tac | tac | gac | gag | aac | gga | gtc | gag | agg | gat | ctc | ttg | 240 |
| Leu | Gly | Gly | Lys | Tyr | Tyr | Asp | Glu | Asn | Gly | Val | Glu | Arg | Asp | Leu | Leu | |
| 65 | | | | | 70 | | | | | 75 | | | | | 80 | |
| gac | atc | ttg | aag | gaa | aac | ggc | gtg | aac | tgg | atc | agg | ctc | cga | gtg | tgg | 288 |
| Asp | Ile | Leu | Lys | Glu | Asn | Gly | Val | Asn | Trp | Ile | Arg | Leu | Arg | Val | Trp | |
| | | | | 85 | | | | | 90 | | | | | 95 | | |
| aac | gat | cct | tat | gac | gaa | cag | ggt | agg | cct | tat | gga | gga | ggc | aac | tgt | 336 |
| Asn | Asp | Pro | Tyr | Asp | Glu | Gln | Gly | Arg | Pro | Tyr | Gly | Gly | Gly | Asn | Cys | |
| | | | 100 | | | | | 105 | | | | | 110 | | | |
| gat | ctc | cct | cgc | atg | acc | gac | ttc | gca | gca | aag | gcg | aag | gcg | aaa | ggc | 384 |
| Asp | Leu | Pro | Arg | Met | Thr | Asp | Phe | Ala | Ala | Lys | Ala | Lys | Ala | Lys | Gly | |
| | | 115 | | | | | 120 | | | | | 125 | | | | |
| ttc | gga | gtg | ttg | att | gat | ttc | cac | tat | tcg | gat | tgg | tgg | gca | gac | ccc | 432 |
| Phe | Gly | Val | Leu | Ile | Asp | Phe | His | Tyr | Ser | Asp | Trp | Trp | Ala | Asp | Pro | |
| | 130 | | | | | 135 | | | | | 140 | | | | | |
| tcg | aaa | cag | tcg | aag | ccc | aag | gcc | tgg | gcc | aac | ctc | tcg | tac | ccc | gag | 480 |
| Ser | Lys | Gln | Ser | Lys | Pro | Lys | Ala | Trp | Ala | Asn | Leu | Ser | Tyr | Pro | Glu | |
| 145 | | | | | 150 | | | | | 155 | | | | | 160 | |
| ctc | gtg | gaa | gcg | gtc | tat | aac | tgg | acc | tac | aac | gcg | ttg | aag | tac | atg | 528 |
| Leu | Val | Glu | Ala | Val | Tyr | Asn | Trp | Thr | Tyr | Asn | Ala | Leu | Lys | Tyr | Met | |
| | | | | 165 | | | | | 170 | | | | | 175 | | |
| gcc | gag | cac | aac | gca | ttg | ccc | gat | atg | gtg | cag | atc | gga | aac | gag | att | 576 |
| Ala | Glu | His | Asn | Ala | Leu | Pro | Asp | Met | Val | Gln | Ile | Gly | Asn | Glu | Ile | |
| | | | 180 | | | | | 185 | | | | | 190 | | | |
| aac | aac | ggc | ttc | ctc | tgg | cct | gat | ggc | tcg | gca | gcc | aac | tgg | aca | cag | 624 |
| Asn | Asn | Gly | Phe | Leu | Trp | Pro | Asp | Gly | Ser | Ala | Ala | Asn | Trp | Thr | Gln | |

```
              195                 200                 205
ttc gtc ggt ttg ttg aaa gca gcc att tcg gca gtg aaa gac gtg aac      672
Phe Val Gly Leu Leu Lys Ala Ala Ile Ser Ala Val Lys Asp Val Asn
    210                 215                 220 ccc aac atc aag att gtc atc cat ctc gca gga gtc aag gcg gat ttc      720
Pro Asn Ile Lys Ile Val Ile His Leu Ala Gly Val Lys Ala Asp Phe
225                 230                 235                 240 tac atc aac ttc att gac agg ttg atc aac tcc gga gtc tcc ttc gac      768
Tyr Ile Asn Phe Ile Asp Arg Leu Ile Asn Ser Gly Val Ser Phe Asp
                245                 250                 255 gtc atc gca atc tcg ttc tat ccc tat tgg cat ggt acc atg gac gac      816
Val Ile Ala Ile Ser Phe Tyr Pro Tyr Trp His Gly Thr Met Asp Asp
            260                 265                 270 ttc agg aac ttg gtg cgc act ctc gtg cag agg tac gat aag aag atc      864
Phe Arg Asn Leu Val Arg Thr Leu Val Gln Arg Tyr Asp Lys Lys Ile
        275                 280                 285 ctc gtc gca gag acc gcg tac gcc tgg acc ctc gat gat tcc gat gga      912
Leu Val Ala Glu Thr Ala Tyr Ala Trp Thr Leu Asp Asp Ser Asp Gly
    290                 295                 300 cac ccg aac att ttc ggt tcg agg gac ctc gag gtc aag gga ggt tac      960
His Pro Asn Ile Phe Gly Ser Arg Asp Leu Glu Val Lys Gly Gly Tyr
305                 310                 315                 320 aaa gcc tcg atc cag gga cag gcc tcg ttc atc cgg gac ctc atc gca     1008
Lys Ala Ser Ile Gln Gly Gln Ala Ser Phe Ile Arg Asp Leu Ile Ala
                325                 330                 335 gca ctc tac gag gag ggt aag gat aaa gca ctc ggc atc ttc tac tgg     1056
Ala Leu Tyr Glu Glu Gly Lys Asp Lys Ala Leu Gly Ile Phe Tyr Trp
            340                 345                 350 ggt gca acc tgg att cct tat cct ggt gcc gga tgg aag act ggc gaa     1104
Gly Ala Thr Trp Ile Pro Tyr Pro Gly Ala Gly Trp Lys Thr Gly Glu
        355                 360                 365 gga aac ccc tgg gag aac cag gca ttg ttc gac ttc aac ggt agg gcc     1152
Gly Asn Pro Trp Glu Asn Gln Ala Leu Phe Asp Phe Asn Gly Arg Ala
    370                 375                 380 ttg cct tcc ctc aag gtc ttc agg ctc gtg tac gaa gcc cag ccc gtc     1200
Leu Pro Ser Leu Lys Val Phe Arg Leu Val Tyr Glu Ala Gln Pro Val
385                 390                 395                 400 gag atc aaa cct ttg gaa ctc taa                                     1224
Glu Ile Lys Pro Leu Glu Leu
                405
```

<210> SEQ ID NO 12
<211> LENGTH: 407
<212> TYPE: PRT
<213> ORGANISM: Artificial Sequence
<220> FEATURE:
<223> OTHER INFORMATION: Synthetic Construct

<400> SEQUENCE: 12

```
Met Arg Leu Gln Lys Asp Phe Asp Arg Val Met Gly Ile Ile Leu Met
1               5                   10                  15

Ile Leu Ile Leu Ala Ile Pro Ser Leu Gln Ile Cys Asn Lys Ser Tyr
            20                  25                  30

Thr Glu Gly Asp Pro Val Ile Ile Asn Pro Val Pro Gly Leu Pro Val
        35                  40                  45

Asp Phe Ile Arg Gly Val Asp Ala Ser Glu Ala Pro Trp Ile Ile Glu
    50                  55                  60

Leu Gly Gly Lys Tyr Tyr Asp Glu Asn Gly Val Glu Arg Asp Leu Leu
65                  70                  75                  80
```

Asp Ile Leu Lys Glu Asn Gly Val Asn Trp Ile Arg Leu Arg Val Trp
                85                  90                  95

Asn Asp Pro Tyr Asp Glu Gln Gly Arg Pro Tyr Gly Gly Asn Cys
            100                 105                 110

Asp Leu Pro Arg Met Thr Asp Phe Ala Ala Lys Ala Lys Ala Lys Gly
            115                 120                 125

Phe Gly Val Leu Ile Asp Phe His Tyr Ser Asp Trp Trp Ala Asp Pro
130                 135                 140

Ser Lys Gln Ser Lys Pro Lys Ala Trp Ala Asn Leu Ser Tyr Pro Glu
145                 150                 155                 160

Leu Val Glu Ala Val Tyr Asn Trp Thr Tyr Asn Ala Leu Lys Tyr Met
                165                 170                 175

Ala Glu His Asn Ala Leu Pro Asp Met Val Gln Ile Gly Asn Glu Ile
            180                 185                 190

Asn Asn Gly Phe Leu Trp Pro Asp Gly Ser Ala Ala Asn Trp Thr Gln
            195                 200                 205

Phe Val Gly Leu Leu Lys Ala Ala Ile Ser Ala Val Lys Asp Val Asn
210                 215                 220

Pro Asn Ile Lys Ile Val Ile His Leu Ala Gly Val Lys Ala Asp Phe
225                 230                 235                 240

Tyr Ile Asn Phe Ile Asp Arg Leu Ile Asn Ser Gly Val Ser Phe Asp
                245                 250                 255

Val Ile Ala Ile Ser Phe Tyr Pro Tyr Trp His Gly Thr Met Asp Asp
            260                 265                 270

Phe Arg Asn Leu Val Arg Thr Leu Val Gln Arg Tyr Asp Lys Lys Ile
            275                 280                 285

Leu Val Ala Glu Thr Ala Tyr Ala Trp Thr Leu Asp Asp Ser Asp Gly
290                 295                 300

His Pro Asn Ile Phe Gly Ser Arg Asp Leu Glu Val Lys Gly Gly Tyr
305                 310                 315                 320

Lys Ala Ser Ile Gln Gly Gln Ala Ser Phe Ile Arg Asp Leu Ile Ala
                325                 330                 335

Ala Leu Tyr Glu Glu Gly Lys Asp Lys Ala Leu Gly Ile Phe Tyr Trp
            340                 345                 350

Gly Ala Thr Trp Ile Pro Tyr Pro Gly Ala Gly Trp Lys Thr Gly Glu
            355                 360                 365

Gly Asn Pro Trp Glu Asn Gln Ala Leu Phe Asp Phe Asn Gly Arg Ala
370                 375                 380

Leu Pro Ser Leu Lys Val Phe Arg Leu Val Tyr Glu Ala Gln Pro Val
385                 390                 395                 400

Glu Ile Lys Pro Leu Glu Leu
                405

<210> SEQ ID NO 13
<211> LENGTH: 21
<212> TYPE: DNA
<213> ORGANISM: Artificial Sequence
<220> FEATURE:
<223> OTHER INFORMATION: Synthetic construct

<400> SEQUENCE: 13
cccttgtcga tgcgatgtat c                                         21

<210> SEQ ID NO 14
<211> LENGTH: 21
<212> TYPE: DNA

<213> ORGANISM: Artificial Sequence
<220> FEATURE:
<223> OTHER INFORMATION: Synthetic construct

<400> SEQUENCE: 14
atcctcaatt ccgtcggtcg a                     21

<210> SEQ ID NO 15
<211> LENGTH: 309
<212> TYPE: PRT
<213> ORGANISM: Bacillus species

<400> SEQUENCE: 15

```
Ala Asn Ser Gly Phe Tyr Val Ser Gly Thr Thr Leu Tyr Asp Ala Asn
1               5                   10                  15

Gly Asn Pro Phe Val Met Arg Gly Ile Asn His Gly His Ala Trp Tyr
            20                  25                  30

Lys Asp Gln Ala Thr Thr Ala Ile Glu Gly Ile Ala Asn Thr Gly Ala
        35                  40                  45

Asn Thr Val Arg Ile Val Leu Ser Asp Gly Gly Gln Trp Thr Lys Asp
    50                  55                  60

Asp Ile His Thr Val Arg Asn Leu Ile Ser Leu Ala Glu Asp Asn His
65                  70                  75                  80

Leu Val Ala Val Leu Glu Val His Asp Ala Thr Gly Tyr Asp Ser Ile
                85                  90                  95

Ala Ser Leu Asn Arg Ala Val Asp Tyr Trp Ile Glu Met Arg Ser Ala
            100                 105                 110

Leu Ile Gly Lys Glu Asp Thr Val Ile Ile Asn Ile Ala Asn Glu Trp
        115                 120                 125

Phe Gly Ser Trp Glu Gly Asp Ala Trp Ala Asp Gly Tyr Lys Gln Ala
    130                 135                 140

Ile Pro Arg Leu Arg Asn Ala Gly Leu Asn His Thr Leu Met Val Asp
145                 150                 155                 160

Ala Ala Gly Trp Gly Gln Phe Pro Gln Ser Ile His Asp Tyr Gly Arg
                165                 170                 175

Glu Val Phe Asn Ala Asp Pro Gln Arg Asn Thr Met Phe Ser Ile His
            180                 185                 190

Met Tyr Glu Tyr Ala Gly Gly Asn Ala Ser Gln Val Arg Thr Asn Ile
        195                 200                 205

Asp Arg Val Leu Asn Gln Asp Leu Ala Leu Val Ile Gly Glu Phe Gly
    210                 215                 220

His Arg His Thr Asn Gly Asp Val Asp Glu Ala Thr Ile Met Ser Tyr
225                 230                 235                 240

Ser Glu Gln Arg Gly Val Gly Trp Leu Ala Trp Ser Trp Lys Gly Asn
                245                 250                 255

Gly Pro Glu Trp Glu Tyr Leu Asp Leu Ser Asn Asp Trp Ala Gly Asn
            260                 265                 270

Asn Leu Thr Ala Trp Gly Asn Thr Ile Val Asn Gly Pro Tyr Gly Leu
        275                 280                 285

Arg Glu Thr Ser Arg Leu Ser Thr Val Phe Thr Gly Gly Gly Ser Asp
    290                 295                 300

Gly Gly Thr Ser Pro
305
```